(12) United States Patent
Zheng et al.

(10) Patent No.: US 10,351,830 B2
(45) Date of Patent: Jul. 16, 2019

(54) CONJUGATES FOR ASSAYS FOR OXYCODONE AND OXYMORPHONE

(71) Applicant: Siemens Healthcare Diagnostics Inc., Tarrytown, NY (US)

(72) Inventors: Yi Feng Zheng, Wilmington, DE (US); Yali Yang, Bear, DE (US); Guoping Wang, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 121 days.

(21) Appl. No.: 15/536,279

(22) PCT Filed: Dec. 11, 2015

(86) PCT No.: PCT/US2015/065215
§ 371 (c)(1),
(2) Date: Jun. 15, 2017

(87) PCT Pub. No.: WO2016/100113
PCT Pub. Date: Jun. 23, 2016

(65) Prior Publication Data
US 2017/0362579 A1    Dec. 21, 2017

Related U.S. Application Data

(60) Provisional application No. 62/093,129, filed on Dec. 17, 2014.

(51) Int. Cl.
*G01N 33/58* (2006.01)
*G01N 33/94* (2006.01)
(Continued)

(52) U.S. Cl.
CPC ......... *C12N 9/0006* (2013.01); *C07D 317/58* (2013.01); *C07D 405/12* (2013.01);
(Continued)

(58) Field of Classification Search
CPC .. C07D 489/08; C07D 489/02; C07D 317/58; C07D 405/12; C12Q 1/28; C12N 9/0006;
(Continued)

(56) References Cited

U.S. PATENT DOCUMENTS 6,033,890 A    3/2000    Jakobovits et al.
6,090,567 A    7/2000    Jakobovits et al.
(Continued)

FOREIGN PATENT DOCUMENTS

WO      0078763 A2     12/2000
WO    WO-2011009015 A1 *  1/2011  ........... A61K 31/472
(Continued)

OTHER PUBLICATIONS

International Search Report and Written Opinion of International Application No. PCT/US2015/065215 dated Feb. 23, 2016.
(Continued)

*Primary Examiner* — Shafiqul Haq
(74) *Attorney, Agent, or Firm* — Cynthia G. Tymeson

(57) ABSTRACT

Compositions, methods, and kits are disclosed directed at haptens, immunogens and immunoassays for oxycodone and metabolites thereof. The compounds are exemplified by compounds of the Formula I. The method comprises providing in combination in a medium (i) a sample suspected of containing oxycodone and/or oxycodone metabolites, a compound of the Formula I wherein $R^4$ or $R^5$ is a label, and an antibody for oxycodone or a metabolite thereof. The medium is examined for the presence of a complex comprising the labeled compound of Formula I where the presence of such as complex indicates the presence of oxycodone or oxycodone metabolite in the sample.

6 Claims, 7 Drawing Sheets

(51) Int. Cl.
*G01N 33/535* (2006.01)
*C07K 16/44* (2006.01)
*C07D 317/58* (2006.01)
*C12N 9/04* (2006.01)
*C07D 489/02* (2006.01)
*C07D 489/08* (2006.01)
*C07D 405/12* (2006.01)
*C12Q 1/28* (2006.01)
*G01N 33/569* (2006.01)

(52) U.S. Cl.
CPC ......... *C07D 489/02* (2013.01); *C07D 489/08* (2013.01); *C07K 16/44* (2013.01); *C12Q 1/28* (2013.01); *G01N 33/535* (2013.01); *G01N 33/56911* (2013.01); *G01N 33/581* (2013.01); *G01N 33/94* (2013.01); *G01N 33/9486* (2013.01)

(58) Field of Classification Search
CPC .. C07K 16/44; G01N 33/9486; G01N 33/581; G01N 33/535; G01N 33/94; G01N 33/56911
See application file for complete search history.

(56) References Cited

U.S. PATENT DOCUMENTS

| | | |
|---|---|---|
| 6,455,288 B1 | 9/2002 | Jakobovits et al. |
| 6,991,911 B2 | 1/2006 | Zheng et al. |
| 7,022,492 B2 | 4/2006 | Zheng et al. |
| 7,026,134 B2 | 4/2006 | Lamont et al. |
| 7,863,427 B2 | 1/2011 | Zheng et al. |
| 2003/0157565 A1 | 8/2003 | Lamont et al. |
| 2004/0204434 A1 | 10/2004 | Shafer et al. |
| 2007/0088162 A1 | 4/2007 | Snuparek et al. |
| 2011/0313163 A1* | 12/2011 | Hudlicky ............ C07D 221/22 546/39 |

FOREIGN PATENT DOCUMENTS

| | | |
|---|---|---|
| WO | 2013116088 A1 | 8/2013 |
| WO | 2014152657 A1 | 9/2014 |

OTHER PUBLICATIONS

Findlay et al., "Relationships between Immunogen Structure and Antisera Specificity in the Narcotic Alkaloid Series", 1981, Clinical Chemistry, vol. 27, No. 9, pp. 1524-1535.

Pravetoni et al.,"Reduced Antinociception of Opioids in Rats and Mice by Vaccination with Immunogens Containing Oxycodone and Hydrocodone Haptens", 2013, Journal of Medicinal Chemistry, vol. 56 No. 3, pp. 915-923.

European Search Report and Written Opinion of European Application No. 15870757.0 dated Nov. 3, 2017.

* cited by examiner

Oxycodone

Oxymorphone

Noroxycodone

Norhydromorphone

CONJUGATES FOR ASSAYS FOR OXYCODONE AND OXYMORPHONE

The subject application claims benefit under 35 USC § 119(e) of U.S. Provisional Application No. 62/093,129, filed Dec. 17, 2014. The entire contents of the above-referenced patent application are hereby expressly incorporated herein by reference.

BACKGROUND

This invention relates to compositions, methods and kits for detecting the presence and/or amounts of certain narcotic analgesics in samples suspected of containing the same. In particular, the present invention relates to homogeneous immunoassays and compositions of matter that are useful in conducting immunoassays for oxycodone and its metabolites such as, for example, oxymorphone. Homogeneous immunoassays have the advantage of not requiring separation steps. Such assays, however, are limited by the difficulty of providing antibodies that will modulate the activity of a label that is normally bound to the antibodies or an analog of the analyte. The present invention overcomes these difficulties and provides immunogenic conjugates for preparation of antibodies and label conjugates such as, for example, glucose-6-phosphate dehydrogenase (G6PDH) conjugates, useful in immunoassays for oxycodone and its metabolites.

The clinical diagnostic field has seen a broad expansion over the years, both as to the variety of materials of interest that may be readily and accurately determined, as well as the methods for the determination. Over the last few decades, testing for therapeutic drugs and drugs of abuse has become commonplace. This testing is not only for the monitoring of criminal offenders and drug addicts, but employers also use it for the screening of workers. Immunoassays based on the reaction of an antibody with an antigen have been extensively investigated for this purpose. Some categories of immunoassays include a radioimmunoassay, using a radioactive isotope, an enzyme-based immunoassay (EIA) using an enzyme, and luminescence assays, using fluorescent labels, e.g., fluorescence polarization, and chemiluminescent labels.

The clinically important and potent analgesic oxycodone is a narcotic analgesic generally indicated for relief of moderate to severe pain. Oxycodone is available as a single ingredient medication in immediate release and controlled release forms. Oxycodone is also formulated with non-narcotic ingredients such as non-steroidal anti-inflammatory drugs (NSAIDs) and acetaminophen and/or with other materials to reduce side effects of oxycodone.

There is, therefore, a need for assays for the detection of oxycodone and its major metabolites such as, for example, oxymorphone. The assays should be able to detect these drugs in order to monitor and treat patients. Antibodies bind to label conjugates in accordance with the principles described thereby providing requisite modulation of signal from the label of the conjugates by the binding of antibodies to the conjugate.

SUMMARY

Some examples in accordance with the principles described herein are directed to a compound of the Formula I:

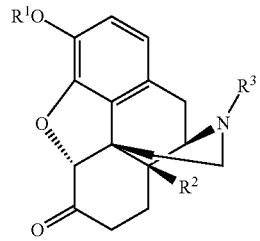

wherein:
$R^1$ is H or lower alkyl,
$R^2$ is H or OH, and
$R^3$ is
(i) $-C(O)-(CH_2)_a-(NH-C(O)-(CH_2)_b)_cR^4$, wherein a is an integer from 1 to 10, b is an integer from 1 to 10 and c is 0 or an integer from 1 to 5, and wherein $R^4$ is halogen, an immunogenic carrier, or a label; or

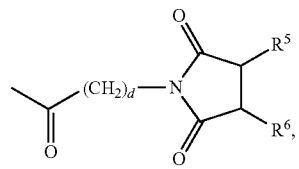

wherein $R^5$ is an immunogenic carrier or a label and wherein $R^6$ is H or is taken together with $R^5$ to form a carbon-carbon double bond.

Some examples in accordance with the principles described herein are directed to a method for determining an amount of oxycodone or a metabolite thereof in a sample suspected of containing oxycodone or a metabolite thereof. A combination is provided in a medium. The combination comprises the sample suspected of containing oxycodone or a metabolite thereof, an antibody for oxycodone or a metabolite thereof, and a compound of the Formula I:

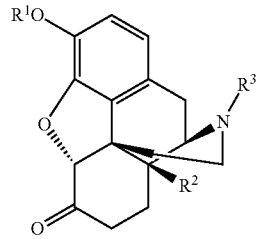

wherein:
$R^1$ is H or lower alkyl,
$R^2$ is H or OH, and
$R^3$ is
(i) $-C(O)-(CH_2)_a-(NH-C(O)-(CH_2)_b)_cR^4$, wherein a is an integer from 1 to 10, b is an integer from 1 to 10 and c is 0 or an integer from 1 to 5, and wherein $R^4$ is a label; or

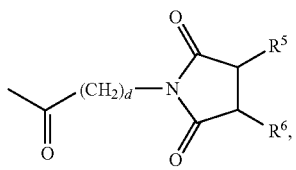

wherein R⁵ is a label and wherein R⁶ is H. The medium is examined for an amount of a complex comprising the antibody and the compound of Formula I, where the amount of the complex indicates the amount of oxycodone or a metabolite thereof in the sample.

Some examples in accordance with the principles described herein are directed to a kit for determining an amount of oxycodone or a metabolite thereof in a sample suspected of containing oxycodone or a metabolite thereof. The kit comprises an antibody for oxycodone or a metabolite thereof and a compound of the Formula I:

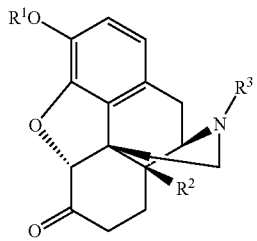

wherein:
  $R^1$ is H or lower alkyl,
  $R^2$ is H or OH, and
  $R^3$ is
  (i) $-C(O)-(CH_2)_a-(NH-C(O)-(CH_2)_b)_c R^4$,
    wherein a is an integer from 1 to 10, b is an integer from 1 to 10 and c is 0 or an integer from 1 to 5, and wherein $R^4$ is a label; or

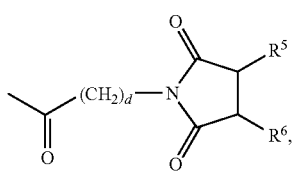

wherein R⁵ is a label and wherein R⁶ is H.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Figure 1:
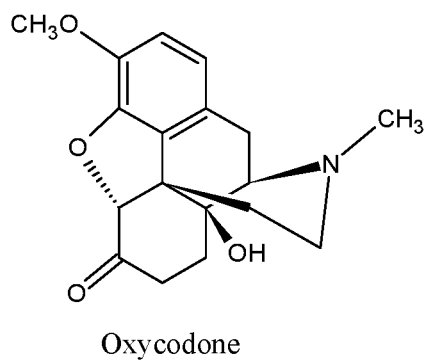
FIG. 1 represents the structure of oxycodone.
Figure 2:
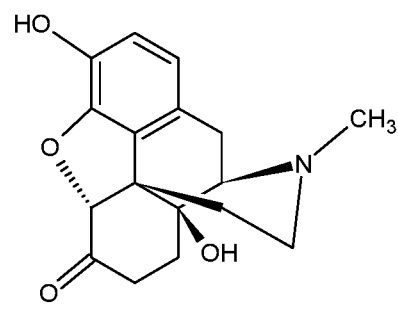
FIG. 2 represents the structure of oxymorphone.
Figure 3:
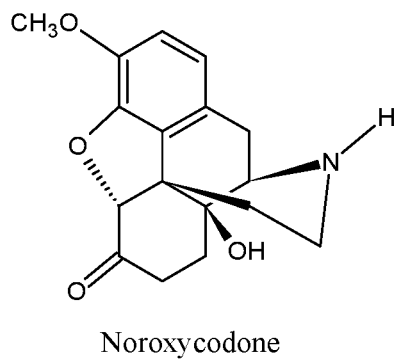
FIG. 3 represents the structure of noroxycodone.
Figure 4:
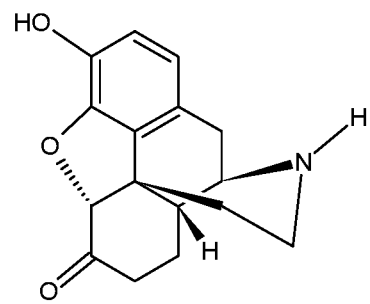
FIG. 4 represents the structure of norhydromorphone.

Some examples in accordance with the principles described herein relate to methods for immunoassay of the analytes oxycodone and oxycodone metabolites such as, for example, oxymorphone. One example in accordance with the principles described herein relates to the use of derivatives of oxycodone or derivatives of one of its metabolites in a signal producing system. The invention also relates to the use of immunogens of oxycodone or its metabolites in producing antibodies for capture of such analytes.

Some examples in accordance with the principles described herein relate to the syntheses of haptens, immunogens, signal conjugates and bio-conjugates of oxycodone and metabolites thereof by linking to the nitrogen atom of the oxycodone molecule or to the nitrogen atom of the oxycodone metabolite molecule by means of a linking group.

The term "derivative" refers to a molecule conjugated to another molecule.

The term "conjugate" refers to a molecule comprised of two or more substructures bound together, optionally through a linking group, to form a single structure. The binding can be made either by a direct connection (e.g. a chemical bond) between the subunits or by use of a linking group. Within the context of the present invention, a conjugate comprises oxycodone or an oxycodone metabolite and a label protein such as an enzyme such as, for example, G6PDH, alkaline phosphatase, β-galactosidase and horse radish peroxidase or a conjugate that comprises oxycodone or an oxycodone metabolite and a chemical label such as a fluorescent, luminescent or colorimetric molecule.

The term "conjugated" or "conjugation" refers to any process wherein two subunits are linked together to form a conjugate. The conjugation process can be comprised of any number of steps.

The phrase "linking group" refers to a chemical moiety that may comprise, not counting hydrogen, about 2 to about 50 atoms, or about 2 to about 20 atoms, or about 2 to about 15 atoms, or about 2 to about 10 atoms, or about 2 to about 5 atoms, or about 3 to about 20 atoms, or about 3 to about 15 atoms, or about 3 to about 10 atoms, or about 3 to about 5 atoms, or about 5 to about 20 atoms, or about 5 to about 15 atoms, or about 5 to about 10 atoms, for example, each independently selected from the group consisting of carbon, oxygen, sulfur, nitrogen, and phosphorous. The linking group may comprise a chain of from 2 to about 40 atoms, or about 2 to about 20 atoms, or about 2 to about 15 atoms, or about 2 to about 10 atoms, or about 2 to about 5 atoms, or about 3 to about 10 atoms, or about 3 to about 5 atoms, or 3 to about 30 atoms, each independently selected from the group consisting of carbon, oxygen, sulfur, nitrogen, and phosphorous. In some examples, part or all of the linking group may be a portion of the molecule being linked such as, but not limited to, an amino acid residue on a poly(amino acid), for example.

The number of heteroatoms in the linking group may be in the range from 0 to about 20, or 1 to about 15, or about 2 to about 10, or 2 to 5. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

In some examples, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed.

The phrase "metabolite of oxycodone" or "oxycodone metabolite" or "oxycodone or metabolites thereof" refers to compounds formed by metabolism of oxycodone by one of multiple metabolic pathways to produce one or more keto-metabolites including, but not limited to, noroxycodone, noroxymorphone, norhydrocodone, norhydromorphone, and oxymorphone, for example. The resulting compounds may further be glucuronidated; for example, oxymorphone is observed as a glucuronide. Noroxycodone (produced by N-demethylation of oxycodone) and noroxymorphone are the major circulating metabolites. O-demethylation of oxycodone yields oxymorphone. Furthermore, the keto group of oxycodone or the keto-metabolites may be reduced to a hydroxy group. For example, oxycodone can be metabolized to α- and β-oxycodol, oxymorphone can be metabolized to α- and β-oxymorphol and noroxycodone can be metabolized to α- and β-noroxycodol.

Compounds

An example of compounds in accordance with the principles described herein is a compound of Formula I:

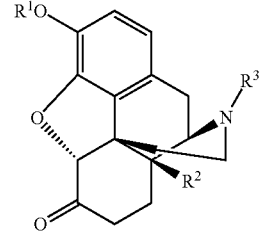

I wherein:
$R^1$ is H or lower alkyl,
$R^2$ is H or OH, and
$R^3$ is
(i) —C(O)—(CH$_2$)$_a$—(NH—C(O)—(CH$_2$)$_b$)$_c$R$^4$,
wherein
a is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;
b is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and
c is 0 or an integer from 1 to 5, or 1 to 4, or 1 to 3, or 1 to 2, or 2 to 5, or 2 to 4, or 2 to 3, or 3 to 5, or 3 to 4, or 4 to 5, for example; and
wherein R$^4$ is halogen, an immunogenic carrier, or a label; or

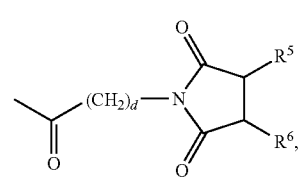

(ii)

wherein R$^5$ is an immunogenic carrier or a label and R$^6$ is H, or wherein R$^5$ and R$^6$ are taken together to form a carbon-carbon double bond.

The term "lower alkyl" refers to alkyl wherein the number of carbon atoms in the organic radical is 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10. Examples of lower alkyl, by way of illustration and not limitation, include methyl, ethyl, n-propyl, iso-propyl, n-butyl, isobutyl, tert-butyl, n-pentyl, and iso-pentyl, for example.

The term "halogen" refers to one or more of bromine, chlorine, iodine and fluorine.

The phrase "immunogenic carrier" refers to molecules that render haptens capable of inducing an immune response in a host. The conjugate of the immunogenic carrier and the hapten may be injected into an organism capable of eliciting an immune response such as, but not limited to, a mammal, an avian (e.g., chicken or pigeon), an amphibian, or a reptile; or the conjugate may be used to inoculate an in vitro sample (mammalian, including human, avian, amphibian or reptile) or otherwise may be employed in a technique to produce a binding partner for the hapten. The immunogenic carriers include poly(amino acid) immunogenic compounds and non-poly(amino acid) immunogenic compounds as well as supports.

The term "hapten" refers to substance that can react specifically with an antibody but by itself is incapable of eliciting an immune response in a host.

The phrase "binding partner" refers to a molecule that is a member of a specific binding pair, which is one of two different molecules that specifically binds to and is thereby defined as complementary with the other molecule. For example, one member of the specific binding pair may have an area on the surface or in a cavity that specifically binds to a particular spatial and polar organization of the other member of the specific binding pair. The binding partner may be, by way of illustration and not limitation, an antibody or an aptamer (e.g., nucleic acid aptamer or peptide aptamer), for example.

In one example, an immunogenic carrier may be employed as an immunogen to induce an immune response and elicit production of a binding partner for a hapten. Other techniques include phage display and in vitro selection. Immunogenic carriers are also sometimes referred to as antigenic carriers. In some examples in accordance with the principles described herein, immunogens comprising immunogenic carriers, including poly(amino acid) and non-poly(amino acid) immunogenic carriers, are synthesized and used to prepare antibodies. Haptens are compounds capable of binding specifically to corresponding antibodies, but do not themselves act as immunogens (or antigens) for preparation of the antibodies. Consequently, a hapten is linked to an immunogenic carrier, which may be employed, for example, to raise antibodies.

The molecular weight range (in Daltons) for poly(amino acids) that are immunogenic carriers is about 5,000 to about 10,000,000, or about 20,000 to about 600,000, or about 25,000 to about 250,000, for example. "Poly(amino acid) immunogenic carrier moieties" include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), for example. "Non-poly(amino acid) immunogenic carrier moieties" include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier moiety may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

As used herein, the term "label" includes poly(amino acid) labels and non-poly(amino acid) labels. The term "poly(amino acid) label" includes labels that are proteins such as, but not limited to, enzymes, antibodies, peptides, and immunogens, for example. With label proteins such as, for example, enzymes, the weight average molecular weight range will be from about 10,000 to about 600,000 or from about 10,000 to about 300,000. There is usually at least one compound in accordance with the principles described herein (analog group) per about 200,000 molecular weight, or at least about 1 per about 150,000 molecular weight, or at least about 1 per about 100,000 molecular weight, or at least about 1 per about 50,000 molecular weight, or at least about 1 per 40,000, molecular weight, or at least about 1 per 30,000 molecular weight, or at least 1 per 20,000 molecular weight, or at least one per 10,000 molecular, or at least one per 5,000 molecular weight, for example, of the protein. In the case of enzymes, the number of analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase (G6PDH) and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

As used herein, the term "non-poly(amino acid) labels" includes those labels that are not proteins. The non-poly (amino acid) label is capable of being detected directly or is detectable through a reaction that produces a detectable signal. The non-poly(amino acid) label can be isotopic or non-isotopic and can be, by way of illustration and not limitation, a radioisotope, a luminescent compound (which includes, but is not limited to fluorescent compounds and chemiluminescent compounds, for example), a polynucleotide coding for a catalyst, a promoter, a dye, a coenzyme, an enzyme substrate, a radioactive group, a small organic molecule (molecular weight 200 to 2,000), a particle, and an amplifiable polynucleotide sequence, for example.

The phrase "small organic molecule" refers to a compound of molecular weight of about 200 to about 2,000, or about 200 to about 1,500, or about 200 to about 1,000, or about 200 to about 500. Such "small organic molecules" include, but are not limited to, biotin, fluorescent molecules (such as fluorescein and rhodamine, for example), chemiluminescent molecules, and dinitrophenol, for example. A binding partner for a small organic molecule is a molecule that specifically recognizes and binds to the small molecule. Binding partners for a small molecule are defined by the nature of the small molecule and include, but are not limited to, avidin, streptavidin, antibody for the small organic molecule (which include, but are not limited to, antibody for a fluorescent molecule (such as antibody for fluorescein and antibody for rhodamine, for example), antibody for a chemiluminescent molecule, and antibody for dinitrophenol, for example.

As used herein, the terms "non-label poly(amino acid)" and "non-immunogenic carrier poly(amino acid)" refer to poly(amino acids) that are not normally considered labels or immunogenic carriers although such moieties may be labels or immunogenic carriers in certain circumstances. For example, an antibody may not be considered a label but may be a label if the antibody is modified to include a signal producing moiety or part of a signal producing system. Furthermore, an antibody may not be considered as an immunogenic carrier but is nonetheless capable of being an immunogenic carrier in certain circumstances because of it high molecular weight.

In some examples the non-poly(amino acid) label may be selected from the group consisting of supports, magnetic particles, acridinium esters, a combination of magnetic particles and acridinium esters (such as, for example, acridinium ester labeled paramagnetic particles), chemiluminescent particles and sensitizer particles.

The term "covalent" refers to attachment of molecules such as by a direct connection, e.g., a chemical bond between the molecules or between the molecules and a linking group. The term "non-covalent" refers to attachment of molecules involving specific binding between complementary specific binding pair (sbp) members that are attached to the molecules.

In some examples compounds in accordance with the principles described herein may be associated with a support, for example, by covalent or non-covalent binding. As mentioned above, in some examples in accordance with the principles described herein, $R^4$ or $R^5$ may be a support, which may be comprised of an organic or inorganic, solid or fluid, water insoluble material and which may be transparent or partially transparent. The support can have any of a number of shapes, such as, but not limited to, a particle (particulate support) including bead, a film, a membrane, a tube, a well, a strip, a rod, a fiber, or a planar surface such as, e.g., a plate or paper, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as, by way of illustration and not limitation, nitrocellulose, cellulose acetate, poly (vinyl chloride), polyacrylamide, polyacrylate, polyethylene, polypropylene, poly(4 methylbutene), polystyrene, polymethacrylate, poly(ethylene terephthalate), nylon, poly(vinyl butyrate), for example, either used by themselves or in conjunction with other materials. The support may or may not be further labeled with a dye, catalyst or other detectable group, for example.

In some examples in accordance with the principles described herein, the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, streptococcus, *Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

Magnetic particles include paramagnetic particles, ferromagnetic particles and diamagnetic particles. Such particles include, but are not limited to, transition metals of periods 4-7 of the Periodic Table including chromium, copper, cobalt, aluminum, manganese, iron, and nickel, for example.

Chemiluminescent particles are particles that have associated therewith a chemiluminescent compound. The phrase "associated therewith" as used herein means that a compound such as, for example, a chemiluminescent compound and a particle may be associated by direct or indirect bonding, adsorption, absorption, incorporation, or solution, for example. Examples of chemiluminescent compounds that may be utilized are those set forth in U.S. Pat. Nos. 5,340,716 and 6,251,581, the relevant disclosures of which are incorporated herein by reference. In some examples in accordance with the principles described herein, the chemiluminescent compound is a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". In some examples, the chemiluminescent compounds are those that react with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and luminol. Examples of such chemiluminescent compounds that may be utilized are those set forth in U.S. Pat. No. 5,709,994, the relevant disclosure of which is incorporated herein by reference.

Sensitizer particles are particles that have associated therewith a sensitizer compound, which includes, but is not limited to, a photosensitizer compound. Examples of sensitizer compounds that may be utilized are those set forth in U.S. Pat. Nos. 5,340,716 and 6,251,581, the relevant disclosures of which are incorporated herein by reference.

A photosensitizer is a sensitizer for generation of singlet oxygen usually by excitation with light. In some examples, the photosensitizer absorbs at a longer wavelength than the chemiluminescent compound and has a lower energy triplet than the chemiluminescent compound. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200-1100 nm, usually 300-1000 nm, preferably 450-950 nm. Typical photosensitizers include, but are not limited to, acetone, benzophenone, 9-thioxanthone, eosin, 9,10-dibromoanthracene, methylene blue, metallo-porphyrins (e.g., hematoporphyrin), phthalocyanines, chlorophylls, rose bengal, buckminsterfullerene, for example, and derivatives of these compounds. Examples of other photosensitizers are enumerated in N. J. Turro, "Molecular Photochemistry", page 132, W. A. Benjamin Inc., N.Y. 1965. The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate.

In the formulas set forth herein, a squiggle line as a bond indicates that the stereochemistry of the bond is not defined.

Some examples in accordance with the principles described herein are directed to Formula II compounds, which are compounds of Formula I wherein c is 0:

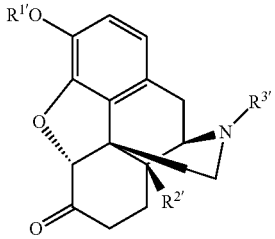

wherein:
$R^{1'}$ is H or methyl,
$R^{2'}$ is H or OH, and
$R^{3'}$ is —C(O)—$(CH_2)_{a'}$—$R^{4'}$, wherein a' is an integer from 1 to 10, or from 1 to 5, or from 1 to 3, and wherein $R^{4'}$ is halogen, an immunogenic carrier, or a label.

One example of compounds of Formula II in accordance with the principles described herein include, by way of illustration and not limitation, compounds of the Formula IIa:

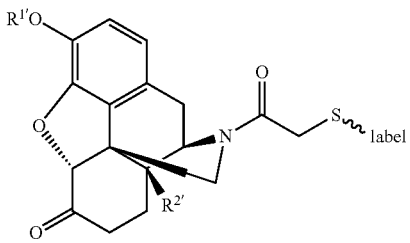

wherein:
$R^{1'}$ is H or methyl,
$R^{2'}$ is H or OH, and
label is selected from the group consisting of dehydrogenases, e.g., glucose-6-phosphate dehydrogenase (G6PDH) and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example. In one example, $R^{1'}$ is methyl, $R^{2'}$ is OH, and label is G6PDH. In one example, $R^{1'}$ is H, $R^{2'}$ is OH, and label is G6PDH. In one example, $R^{1'}$ is methyl, $R^{2'}$ is H, and label is G6PDH. In one example, $R^{1'}$ is H, $R^{2'}$ is OH, and label is G6PDH. In one example, $R^{1'}$ is H, $R^{2'}$ is H, and label is G6PDH.

Some examples in accordance with the principles described herein are directed to Formula III compounds, which are compounds of Formula I wherein c is 1:

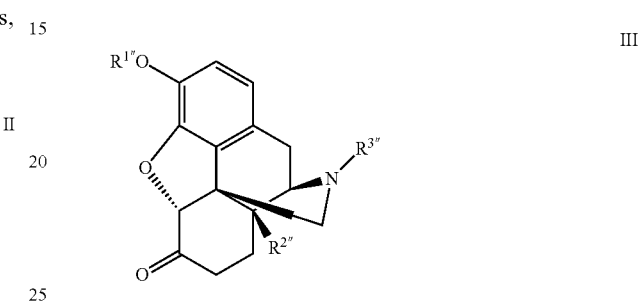

wherein:
$R^{1''}$ is H or methyl,
$R^{2''}$ is H or OH, and
$R^{3''}$ is —C(O)—$(CH_2)_{a''}$—NH—C(O)—$(CH_2)_{b''}$—$R^{4''}$, wherein a'' is an integer from 1 to 10, or from 1 to 5, or from 1 to 3, b'' is an integer from 1 to 10, or from 1 to 5, or from 1 to 3, and wherein $R^{4''}$ is halogen, an immunogenic carrier, or a label.

One example of compounds of Formula III in accordance with the principles described herein include, by way of illustration and not limitation, compounds of the Formula IIIa:

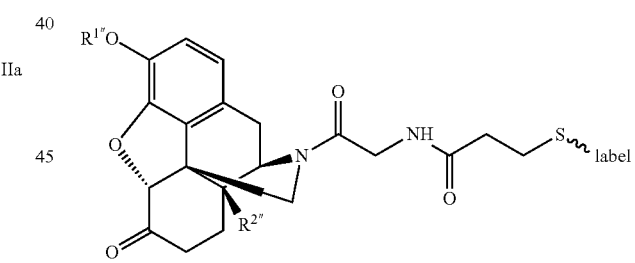

wherein:
$R^{1''}$ is H or methyl,
$R^{2''}$ is H or OH, and label is selected from the group consisting of dehydrogenases, e.g., glucose-6-phosphate dehydrogenase (G6PDH) and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example. In one example, $R^{1'''}$ is methyl, $R^{2'''}$ is OH, and label is G6PDH. In one example, $R^{1'''}$ is H, $R^{2'''}$ is OH, and label is G6PDH. In one example, $R^{1'''}$ is methyl, $R^{2'''}$ is H, and label is G6PDH. In one example, $R^{1'''}$ is H, $R^{2'''}$ is OH, and label is G6PDH. In one example, $R^{1'''}$ is H, $R^{2'''}$ is H, and label is G6PDH.

Some examples in accordance with the principles described herein are directed to Formula IV compounds, which are compounds of Formula I wherein:

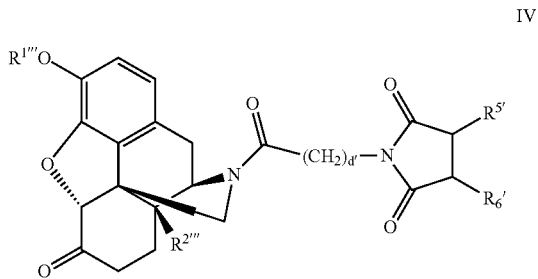

IV wherein:
$R^{1'''}$ is H or methyl,
$R^{2'''}$ is H or OH, and
wherein $R^{5'}$ is halogen, an immunogenic carrier, or a label and $R^{6'}$ is H.

One example of compounds of Formula IV in accordance with the principles described herein include, by way of illustration and not limitation, compounds of the Formula IVa:

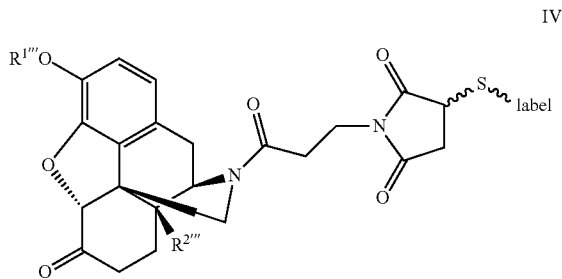

IVa wherein:
$R^{1'''}$ is H or methyl,
$R^{2'''}$ is H or OH, and label is selected from the group consisting of dehydrogenases, e.g., glucose-6-phosphate dehydrogenase (G6PDH) and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example. In one example, $R^{1'''}$ is methyl, $R^{2'''}$ is OH, and label is G6PDH. In one example, $R^{1'''}$ is H, $R^{2'''}$ is OH, and label is G6PDH. In one example, $R^{1'''}$ is methyl, $R^{2'''}$ is H, and label is G6PDH. In one example, $R^{1'''}$ is H, $R^{2'''}$ is OH, and label is G6PDH. In one example, $R^{1'''}$ is H, $R^{2'''}$ is H, and label is G6PDH.

Preparation of Compounds

Examples of methods of preparing compounds that are in accordance with the principles described herein are discussed below by way of illustration and not limitation. Other approaches may be employed to form the above compounds and other compounds consistent with the principles described herein.

One example, by way of illustration and not limitation, of the preparation of compounds in accordance with the principles described herein is set forth below with reference to FIG. 5. The HCl derivative of noroxycodone (X) is reacted with succinimide acetate bromide (XI) in the presence of one or more polar organic solvents such as, for example, an ether such as, e.g., tetrahydrofuran (THF) or 1,4-dioxane; an amide such as, e.g., dimethylformamide (DMF); and an amine such as, e.g., triethylamine or N,N-diisopropylethylamine. The reaction components are subjected to conditions for forming a compound of the Formula XII. In some examples the temperature during the reaction is about 15° C. to about 25° C., or room temperature. The time period of the reaction is about 1 hour to about 4 hours or about 1.5 hours to about 2 hours. The reaction is carried out in an inert atmosphere such as, for example, nitrogen or argon or mixtures of two or more inert gases. The resulting product, which is a mixture of noroxycodone bromoacetamide (XII) and noroxycodone chloroacetamide (XIII) may be subjected to one or more chromatographic techniques such as, for example, thin layer chromatography (TLC), column chromatography, or preparative high performance liquid chromatography (HPLC), and the product is treated with a metal bromide salt such as a bromide salt of sodium, potassium, or lithium, for example, in an polar organic solvent such as, for example, one or more of a ketone such as, e.g., acetone or butanone, under condition for forming the desired noroxycodone bromoacetamide (XII). In some examples the temperature during the reaction is about 45° C. to about 65° C., or about 50° C. to about 60° C. The time period of the reaction is about 20 hours to about 40 hours or about 24 hours to about 30 hours. The reaction is carried out in an inert atmosphere such as, for example, nitrogen or argon or mixtures of two or more inert gases. The resulting product, noroxycodone bromoacetamide (XII), may be subjected to one or more chromatographic technique such as, for example, thin layer chromatography (TLC), column chromatography, or preparative HPLC.

The G6PDH conjugate (XIV) is formed from compound XII by reaction with activated G6PDH. A G6PDH solution is exchanged using a suitable column such as, for example, a SEPHADEX® column, and using a buffer such as, for example, phosphate buffered saline (PBS), 2-(N-morpholino)ethanesulfonic acid (MES) buffer or tris(hydroxymethyl)aminomethane (Tris) buffer. The G6PDH is treated with an activation agent such as, for example, an agent for reduction of disulfide groups of an enzyme to form free sulfhydryl groups or thiols. Agents for reduction of disulfide groups include, but are not limited to, sulfur-containing reducing agents such as, for example, dithiothreitol (DTT), and 2-mercaptoethanol (2ME), dithioerythritol (DTE), cysteine, mercaptoacetic acid, 2-aminoethanethiol, N-acetyl cysteine, for example, or other reducing agents such as, for example, a borohydride, e.g., sodium borohydride or pyridine borane, or a phosphine, e.g., tris-(2-carboxyethyl) phosphine hydrochloride, and bisulfite solutions especially a metabisulfite solution (MBS) or sodium bisulfite, and including combinations of two or more of the above reducing agents that are compatible with one another. Activated G6PDH is combined with compound XII to give compound XIV. The reaction components are subjected to conditions for forming a compound of the Formula XIV. In some examples the temperature during the reaction is about 0° C. to about 10° C., or about 2° C. to about 8° C. The time period of the reaction is about 12 hours to about 24 hours or about 15 hours to about 20 hours. The resulting enzyme conjugate XIV may be subjected to one or more chromatographic techniques such as, for example, column chromatography, TLC, SEPHADEX® gel chromatography, hydrophobic chromatography, affinity chromatography, ion exchange chromatography, gel filtration chromatography, or reversed phase chromatography.

Another example, by way of illustration and not limitation, of the preparation of compounds in accordance with the principles described herein is set forth below with reference to FIG. 6. The HCl derivative of noroxymorphone (XV) is reacted with succinimide acetate bromide (XI) under conditions as described above for the example of FIG. 5. The resulting product, which is a mixture of noroxymorphone bromoacetamide (XVII) and noroxymorphone chloroacetamide (XVIII) may be subjected to one or more chromatographic techniques as discussed above and the product is treated with a metal bromide salt in an polar organic solvent under condition for forming the desired noroxymorphone bromoacetamide (XVII) as described above for the example of FIG. 5.

The G6PDH conjugate (XIX) was formed from compound XVII by reaction with activated G6PDH as discussed above for the example of FIG. 5. The G6PDH is subjected to buffer exchange and then treated with an activation agent as described above. Activated G6PDH is combined with compound XVII to give compound XIX. The reaction components are subjected to conditions for forming a compound of the Formula XIX as described above for the example in FIG. 5. The resulting enzyme conjugate XIX may be subjected to one or more chromatographic techniques as discussed above.

Another example, by way of illustration and not limitation, of the preparation of compounds in accordance with the principles described herein is set forth below with reference to FIG. 7. The HCl derivative of noroxymorphone (XV) is reacted with BA glycine NHS ester (XX) (BA glycine NHS ester is bromoacetyl glycine N-hydroxysuccinimide ester). The reaction is carried out in a polar organic solvent such as, for example, one or more of an ether such as, e.g., THF, an amide such as, e.g., DMF, a ketone such as, e.g., acetone or butanone, under conditions for forming the desired noroxymorphone bromoacetamide (XXI). In some examples the temperature during the reaction is about 15° C. to about 35° C., or about 20° C. to about 25° C. The time period of the reaction is about 15 minutes to about 4 hours, or about 20 minutes to about 2 hours. The reaction is carried out in an inert atmosphere such as, for example, nitrogen or argon or mixtures of two or more inert gases. The resulting product, noroxymorphone bromoacetamide (XXI) may be subjected to one or more of chromatographic technique as discussed above for the example of FIG. 5.

The G6PDH conjugate (XXIII) was formed from compound XXI by reaction with activated G6PDH as discussed above for the example of FIG. 5. The G6PDH is subjected to buffer exchange and then treated with an activation agent as described above. Activated G6PDH is combined with compound XXI to give compound XXIII. The reaction components are subjected to conditions for forming a compound of the Formula XXIII as described above for the example in FIG. 5. The resulting enzyme conjugate XXIII may be subjected to one or more chromatographic techniques as discussed above.

Another example, by way of illustration and not limitation, of the preparation of compounds in accordance with the principles described herein is set forth below with reference to FIG. 8. The HCl derivative of norhydromorphone (XXV) is reacted with BA glycine NHS ester (XX). The reaction is carried out in a polar organic solvent such as, for example, one or more of an ether such as, e.g., THF, an amide such as, e.g., DMF, a ketone such as, e.g., nitrogen or argon or mixtures of two or more inert gases under conditions for forming the desired noroxymorphone bromoacetamide (XXVI). In some examples the temperature during the reaction is about 15° C. to about 35° C., or about 20° C. to about 25° C. The time period of the reaction is about 10 minutes to about 4 hours, or about 20 minutes to about 2 hours. The reaction is carried out in an inert atmosphere such as, for example, nitrogen or argon or mixtures of two or more inert gases. The resulting product, norhydromorphone bromoacetamide (XXVI) may be subjected to one or more of chromatographic technique as discussed above for the example of FIG. 5.

The G6PDH conjugate (XXVIII) was formed from compound XXVI by reaction with activated G6PDH as discussed above for the example of FIG. 5. The G6PDH is subjected to buffer exchange and then treated with an activation agent as described above. Activated G6PDH is combined with compound XXVI to give compound XXVIII. The reaction components are subjected to conditions for forming a compound of the Formula XXVIII as described above for the example in FIG. 5. The resulting enzyme conjugate XXVIII may be subjected to one or more chromatographic techniques as discussed above.

Another example, by way of illustration and not limitation, of the preparation of compounds in accordance with the principles described herein is set forth below with reference to FIG. 9. The HCl derivative of noroxycodone (X) is reacted with 3-maleimidepropanic acid N-hydroxy succinimide (XXX) under conditions as described above for the example of FIG. 7. The resulting product, which is noroxycodone maleimide (XXXI) may be subjected to one or more of chromatographic technique as discussed above for the example of FIG. 5.

The G6PDH conjugate (XXXII) was formed from compound XXXI by reaction with activated G6PDH as discussed above for the example of FIG. 5. The G6PDH is subjected to buffer exchange and then treated with an activation agent as described above. Activated G6PDH is combined with compound XXXI to give compound XXXII. The reaction components are subjected to conditions for forming a compound of the Formula XXXII as described above for the example in FIG. 5. The resulting enzyme conjugate XXXII may be subjected to one or more chromatographic techniques as discussed above.

Another example, by way of illustration and not limitation, of the preparation of compounds in accordance with the principles described herein is set forth below with reference to FIG. 10. The HCl derivative of noroxymorphone (XV) is reacted with 3-maleimidepropanic acid N-hydroxy succinimide (XXX) under conditions as described above for the example of FIG. 7. The resulting product, which is noroxymorphone maleimide (XXXV) may be subjected to one or more of chromatographic technique as discussed above for the example of FIG. 5.

The G6PDH conjugate (XXXVI) was formed from compound XXXV by reaction with activated G6PDH as discussed above for the example of FIG. 5. The G6PDH is subjected to buffer exchange and then treated with an activation agent as described above. Activated G6PDH is combined with compound XXXV to give compound XXXVI. The reaction components are subjected to conditions for forming a compound of the Formula XXXVI as described above for the example in FIG. 5. The resulting enzyme conjugate XXXVI may be subjected to one or more chromatographic as discussed above.

Other compounds in accordance with the principles described herein may be prepared in a manner similar to that described above.

Preparation of Binding Partners

Examples of compounds in accordance with the principles described herein where $R^4$ or $R^5$ is an immunogenic carrier may be employed to prepare binding partners for oxycodone and/or one or more of oxycodone metabolites. Binding partners include, but are not limited to, aptamers for oxycodone and/or one or more of its metabolites, which include, but are not limited to, antibodies specific for oxycodone, antibodies specific for oxymorphone, antibodies specific for noroxycodone, and antibodies specific for norhydromorphone, for example.

Antibodies may be a monoclonal antibodies or a polyclonal antibodies and may include a complete immunoglobulin or fragment thereof, which immunoglobulins include, but are not limited to, various classes and isotypes, such as IgA, IgD, IgE, IgG and IgM, for example. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Antibodies in accordance with the principles described herein may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

Monoclonal antibodies can be prepared by techniques such as preparing continuous hybrid cell lines and collecting the secreted protein (somatic cell hybridization techniques). Monoclonal antibodies may be produced according to the standard techniques of Kohler and Milstein, *Nature* 265: 495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with an immunogen that comprises a compound of Formula I wherein Z is an immunogenic carrier, for example. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as, for example, an enzyme-linked immunosorbent assay (ELISA) or other immunoassays appropriate for screening.

An antibody (prepared from an immunogen in accordance with the principles described herein) with the requisite specificity may be selected by screening methodologies, which include, by way of illustration and not limitation, ELISA, dot blots, Western analysis, and Surface Plasmon Resonance, for example. In this manner an antibody is obtained that binds to oxycodone or to a metabolite of oxycodone and does not bind to any detectable degree to other molecules that are not of interest in a particular assay. In some examples in accordance with the principles described herein, an antibody that binds to oxycodone or to a metabolite of oxycodone has a binding affinity for the oxycodone or to a metabolite of oxycodone of about $10^7$ to about $10^{14}$ liters/mole, or about $10^7$ to about $10^{11}$ liters/mole, or about $10^7$ to about $10^{12}$ liters/mole, or about $10^8$ to about $10^{14}$ liters/mole, or about $10^8$ to about $10^{11}$ liters/mole, or about $10^8$ to about $10^{12}$ liters/mole, for example. The phrase "any detectable degree" means that the antibody that specifically binds to oxycodone or to a metabolite of oxycodone has a binding affinity for a molecule that is not of interest of less than about $10^4$ liters/mole, or less than about $10^3$ liters/mole, or less than about $10^2$ liters/mole, or less than about 10 liters/mole, for example.

In one example, by way of illustration and not limitation, in accordance with the principles described herein, an immunogen, prepared from a compound of Formula I above wherein $R^1$ is methyl, $R^2$ is OH, and $R^4$ or $R^5$ is an immunogenic carrier, is employed to prepare antibodies that are specific for oxycodone, for example.

In another example, by way of illustration and not limitation, in accordance with the principles described herein, an immunogen, prepared from a compound of Formula I above wherein $R^1$ is H, $R^2$ is OH, and $R^4$ or $R^5$ is an immunogenic carrier, is employed to prepare antibodies that are specific for oxymorphone, for example.

In another example, by way of illustration and not limitation, in accordance with the principles described herein, an immunogen, prepared from a compound of Formula I above wherein $R^1$ is H, $R^2$ is H, and $R^4$ or $R^5$ is an immunogenic carrier, is employed to prepare antibodies that are specific for norhydromorphone, for example.

General Description of Assays for Oxycodone and Metabolites of Oxycodone

Some examples in accordance with the principles described herein are directed to methods of determining one or both of the presence and the amount of an analyte in a sample suspected of containing the analyte where the analyte is oxycodone or an oxycodone metabolite. Such assay may be referred to herein as "assays for oxycodone or an oxycodone metabolite."

In an example, by way of illustration and not limitation, of a method for determining oxycodone or a metabolite of oxycodone, a combination is provided that comprises the sample, a binding partner such as, for example, an antibody, for oxycodone or a metabolite of oxycodone and a conjugate of a compound of Formula I wherein $R^4$ or $R^5$ is a label.

As mentioned above, the sample and reagents are provided "in combination in the medium." While the order of addition to the medium may be varied to form the combination, there will be certain preferences for some embodiments of the assay formats described herein. In one example, by way of illustration and not limitation, the order of addition is to add all the materials simultaneously and determine the effect that the assay medium has on the signal from the label as in a homogeneous assay. In another example, by way of illustration and not limitation, each of the reagents, or groups of reagents, can be combined sequentially. In some embodiments, an incubation step may be involved subsequent to each addition as discussed above. In heterogeneous assays, separation and washing steps may also be employed after one or more incubation steps.

The sample to be analyzed is one that is suspected of containing an analyte that is oxycodone or a metabolite of oxycodone. The samples may be biological samples or non-biological samples. Biological samples may be from a mammalian subject or a non-mammalian subject. Mammalian subjects may be, for example, humans or other animal species. Biological samples include, but are not limited to, biological fluids such as whole blood, serum, plasma, sputum, lymphatic fluid, semen, vaginal mucus, feces, urine, spinal fluid, saliva, stool, cerebral spinal fluid, tears, and mucus, for example, and biological tissue such as hair, skin, sections or excised tissues from organs or other body parts, for example. In many instances, the sample is whole blood, plasma or serum. Non-biological samples including, but not limited to, waste streams, for example, may also be analyzed using compounds in accordance with the principles described herein.

The sample can be prepared in any convenient medium, which may be, for example, an assay medium, which is discussed more fully hereinbelow. In some instances a pretreatment may be applied to the sample such as, for example, to lyse blood cells. In some examples, such pretreatment is performed in a medium that does not interfere subsequently with an assay.

The combination in the medium is subjected to conditions for binding of the analyte that is oxycodone or a metabolite of oxycodone and a compound of Formula I, wherein $R^4$ or $R^5$ is a label, to an antibody for the analyte to form a complex. The amount of the complex is measured where the amount of the complex is related to one or both of the presence and amount of the oxycodone or metabolite thereof in the sample.

An assay for oxycodone or a metabolite of oxycodone can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays includes immunoassays using a limited concentration of a compound in accordance with the principles described herein. Another group of immunoassays involves the use of an excess of one or more of the principal reagents such as, for example, an excess of a compound in accordance with the principles described herein. Another group of immunoassays includes separation-free homogeneous assays in which signal from a labeled compound of the Formula I is modulated upon binding of the oxycodone or a metabolite of oxycodone analyte to an antibody for oxycodone or a metabolite of oxycodone. The antibody can be produced in accordance with the principles described herein. The labeled compound of Formula I and the analyte that may be present in the sample compete for binding to the antibody.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"); the Affinity Chromium dioxide Mediated Immuno Assay ("ACMIA") assay format, which is described in U.S. Pat. Nos. 7,186,518, 5,147,529, 5,128,103, 5,158,871, 4,661,408, 5,151,348, 5,302,532, 5,422,284, 5,447,870, and 5,434,051. The relevant portions of the above disclosures are all incorporated herein by reference.

Other assays include acridinium ester label assays such as those discussed in U.S. Pat. Nos. 6,355,803; 6,673,560; 7,097,995 and 7,319,041, the relevant disclosures of which are incorporated herein by reference. A particular example of an acridinium ester label assay is an acridinium ester label immunoassay using paramagnetic particles as a solid phase ("ADVIA" immunoassay). Other assays include the sol particle immunoassay ("SPIA"), the disperse dye immunoassay ("DIA"); the metalloimmunoassay ("MIA"); the enzyme membrane immunoassays ("EMIA"); and luminoimmunoassays ("LIA"). Other types of assays include immunosensor assays involving the monitoring of the changes in the optical, acoustic and electrical properties of the present conjugate upon the binding of oxycodone analyte or oxycodone metabolite analyte. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for oxycodone or a metabolite of oxycodone analyte bound thereto is contacted with a medium containing the sample suspected of containing the analyte and a labeled compound in accordance with the principles described herein. Analyte in the sample competes, for binding to the antibody for the analyte, with the labeled compound. After separating the support and the medium, the label activity of the support or the medium is determined by conventional techniques and is related to the amount of oxycodone or a metabolite of oxycodone analyte in the sample. In a variation of the above competitive heterogeneous assay, the support comprises a compound of the Formula I and the antibody for oxycodone or oxycodone metabolite comprises a label.

In some examples, a sample to be analyzed is combined in an assay medium with an antibody for oxycodone or oxycodone metabolite and labeled compound of the Formula I. The medium is examined for one or both of the presence and amount of a complex comprising the labeled compound of Formula I and the antibody for oxycodone or for oxycodone metabolite analyte where the presence and/or the amount of such complex indicates the presence and/or amount of the oxycodone or oxycodone metabolite analyte in the sample.

The conditions for conducting the assays include carrying out the assay in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include, by way of illustration and not limitation, borate, phosphate, carbonate, TRIS, barbital, PIPES, HEPES, MES, ACES, MOPS, and BICINE, for example. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as, for example, albumins; organic solvents such as, for example, formamide; quaternary ammonium salts; polyanions such as, for example, dextran sulfate; binding enhancers, for example, polyalkylene glycols; polysaccharides such as, for example, dextran or trehalose. The medium may also comprise agents for preventing the formation of blood clots. Such agents are well known in the art and include, but are not limited to, EDTA, EGTA, citrate, heparin, for example. The medium may also comprise one or more preservatives such as, but not limited to, sodium azide, neomycin sulfate, PROCLIN® 300, Streptomycin, for example. The medium may additionally comprise one or more surfactants. Any of the above materials, if employed, is present in a concentration or amount sufficient to achieve the desired effect or function.

One or more incubation periods may be applied to the medium at one or more intervals including any intervals between additions of various reagents employed in an assay including those mentioned above. The medium is usually incubated at a temperature and for a time sufficient for binding of various components of the reagents and binding of oxycodone or oxycodone metabolite in the sample to occur. Moderate temperatures are normally employed for carrying out the method and usually constant temperature, preferably, room temperature, during the period of the measurement. In some examples, incubation temperatures range from about 5° to about 99° C., or from about 15° C. to about 70° C., or from about 20° C. to about 45° C., for example. The time period for the incubation, in some examples, is about 0.2 seconds to about 24 hours, or about 1 second to about 6 hours, or about 2 seconds to about 1 hour, or about 1 minute to about 15 minutes, for example. The time period depends on the temperature of the medium and the rate of binding of the various reagents, which is determined by the association rate constant, the concentration, the binding constant and dissociation rate constant.

In an example of a method for determining oxycodone or oxycodone metabolite analyte in a sample suspected of containing oxycodone or oxycodone metabolite analyte, a combination is provided in a medium where the combination includes the sample, an antibody for oxycodone or for oxycodone metabolite, and a labeled compound of the Formula I where the label is a poly(amino acid) label or a non-poly(amino acid) label. The medium is examined for one or both of the presence and amount of one or both of a complex comprising oxycodone or oxycodone metabolite and the antibody for oxycodone or oxycodone metabolite or a complex comprising the labeled compound of Formula I and antibody for oxycodone or oxycodone metabolite. The presence and/or the amount of one or both of the complexes indicate the presence and/or amount of the oxycodone or oxycodone metabolite analyte in the sample.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light or an activated product, which results in activation of another member of the sps. Such sps members include, by way of illustration and not limitation, first and second enzymes, first and second chemiluminescent compounds, and first and second fluorescent compounds, for example. In a particular example, an induced luminescence immunoassay may be employed. The induced luminescence immunoassay is referred to in U.S. Pat. No. 5,340,716 (Ullman), which disclosure is incorporated herein by reference.

The concentration of the oxycodone or oxycodone metabolite analyte in a sample that may be assayed generally varies from about $10^{-5}$ to about $10^{-17}$ M, or from about $10^{-6}$ to about $10^{-14}$ M, for example. Considerations such as whether the assay is qualitative, semi-quantitative or quantitative (relative to the amount of the oxycodone or oxycodone metabolite analyte present in the sample), the particular detection technique and the expected concentration of the oxycodone or oxycodone metabolite analyte normally determine the concentrations of the various reagents.

The concentrations of the various reagents in the assay medium will generally be determined by the concentration range of interest of the oxycodone or oxycodone metabolite analyte and the nature of the assay, for example. However, the final concentration of each of the reagents is normally determined empirically to optimize the sensitivity of the assay over the range of interest. That is, a variation in concentration of oxycodone or oxycodone metabolite analyte that is of significance should provide an accurately measurable signal difference. Considerations such as the nature of the signal producing system and the nature of the analytes normally determine the concentrations of the various reagents.

As mentioned above, assays for oxycodone or oxycodone metabolite analytes may be carried out using a compound of the Formula I wherein $R^4$ and $R^5$ is a poly(amino acid) label, or a non-poly(amino acid) label or a support.

In one example, by way of illustration and not limitation, of an assay for the detection of oxycodone and/or oxycodone metabolite, an EMIT® assay format is employed. The assay employs an antibody for oxycodone or for an oxycodone metabolite and a compound of the Formula I above wherein $R^4$ or $R^5$ is an enzyme label such as, by way of illustration and not limitation, G6PDH or mutant G6PDH. These agents are combined in an aqueous assay medium together with a sample suspected of containing oxycodone or an oxycodone metabolite. Oxycodone or oxycodone metabolite from the sample competes with the enzyme labeled compound of the Formula I for binding to the antibody for oxycodone or for metabolite of oxycodone. The more of the oxycodone or oxycodone metabolite that is in the sample, the less is the amount of labeled compound of the Formula I that becomes bound to the antibody. Thus, an increase in signal from the enzyme label means that more analyte is present in the sample. After a suitable incubation period, the medium is examined for the presence of a signal from the enzyme. In one example, G6PDH converts oxidized nicotinamide adenine dinucleotide ($NAD^+$) to NADH resulting in an absorbance change that is measured spectrophotometrically. The signal may be related to signal from assays using calibrators containing known amounts of oxycodone or oxycodone metabolite to determine an amount of oxycodone or oxycodone metabolite in the sample.

In another example, by way of illustration and not limitation, of an assay for detection of oxycodone or oxycodone metabolite analyte, an ACMIA assay format is employed. Chrome particles, which are coated with a labeled compound of the Formula I wherein the label is a non-poly (amino acid) label that is the chrome particle (chrome particle reagent), are employed as a first component. A second component is an antibody for oxycodone or oxycodone metabolite analyte. This antibody, crosslinked to a reporter enzyme (for example, β-galactosidase) to form an antibody-enzyme conjugate, is added to a reaction vessel in an excess amount, i.e., an amount greater than that required to bind all of the oxycodone or oxycodone metabolite analyte that might be present in a sample. A sample suspected of containing oxycodone or oxycodone metabolite is treated with an antibody for oxycodone or oxycodone metabolite, which binds to oxycodone or oxycodone metabolite analyte in the sample. The antibody-enzyme conjugate is mixed with sample in the medium to allow the oxycodone or oxycodone metabolite analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of oxycodone or oxycodone metabolite analyte in the sample using calibrators as discussed above.

Examination Step

As discussed above, in one step of an assay method, the medium is examined for the presence of a complex comprising the oxycodone or oxycodone metabolite analyte and antibody for the oxycodone or for oxycodone metabolite and/or a complex comprising a labeled compound of the Formula I and antibody for oxycodone or for oxycodone metabolite. The presence and/or amount of one or both of the complexes indicates the presence and/or amount of the oxycodone or oxycodone metabolite analyte in the sample.

The phrase "measuring the amount of oxycodone or oxycodone metabolite analyte" refers to the quantitative, semiquantitative and qualitative determination of oxycodone or oxycodone metabolite. Methods that are quantitative, semiquantitative and qualitative, as well as all other methods for determining the oxycodone or oxycodone metabolite analyte, are considered to be methods of measuring the amount of the oxycodone or oxycodone metabolite analyte. For example, a method, which merely detects the presence or absence of the oxycodone or oxycodone metabolite analyte in a sample suspected of containing the oxycodone or oxycodone metabolite analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the oxycodone or oxycodone metabolite analyte in the sample. The particular mode of detection depends on the nature of the signal producing system. As discussed above, there are numerous methods by which a label of a signal producing signal can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C., for example. In one approach standard curves are formed using known concentrations of oxycodone or oxycodone metabolite analyte, which are sometimes referred to as calibrators. In addition to calibrators, other controls may be used.

Luminescence or light produced from any label can be measured visually, photographically, actinometrically, spectrophotometrically, such as by using a photomultiplier or a photodiode, or by any other convenient means to determine the amount thereof, which is related to the amount of oxycodone or oxycodone metabolite analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conducting Assays

Kits comprising reagents for conducting assays can be formulated based on the nature of a particular assay. In some examples in accordance with the principles described herein a kit can comprise a binding partner such as, for example, an antibody raised against an immunogen that is a compound of the Formula I wherein $R^4$ or $R^5$ is an immunogenic carrier. In some examples in accordance with the principles described herein, a kit can comprise a reagent that is a compound of the Formula I wherein $R^4$ or $R^5$ is a poly(amino acid) label moiety or a non-poly(amino acid) label moiety including a support. A kit may also include other reagents for conducting a particular assay for oxycodone or oxycodone metabolite analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members, and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a compound reagent in accordance with the principles described herein. The kit can further include a written description of a method utilizing reagents that include a compound reagent in accordance with the principles described herein.

EXAMPLES

Unless otherwise indicated, materials in the experiments below may be purchased from the Sigma-Aldrich Inc. (Milwaukee Wis.). Parts and percentages disclosed herein are by weight to volume unless otherwise indicated. HPLC purification was conducted using an LC-8A (Shimadzu Precision Instruments, Inc., Torrance Calif.). Ultraviolet-visible (UV-Vis) spectroscopy was conducted using a Cary 60 (Agilent Technologies, Palo Alto Calif.). Preparative TLC purification was conducted using TLC plates (20 cm×20 cm, 2000 μm) from Analtech (Newark Del.). $^1$H-NMR spectra were recorded on a Bruker Ultrashiel™-400 (400 MHZ) and a Bruker Ultrashiel™-600 (600 MHz) spectrometers (Bruker Instruments, Billerica, Mass.). Chemical shifts were reported in parts per million (ppm, δ); tetramethylsilane (TMS) or other deuterated solvents were used as the internal references.

Figure 5:
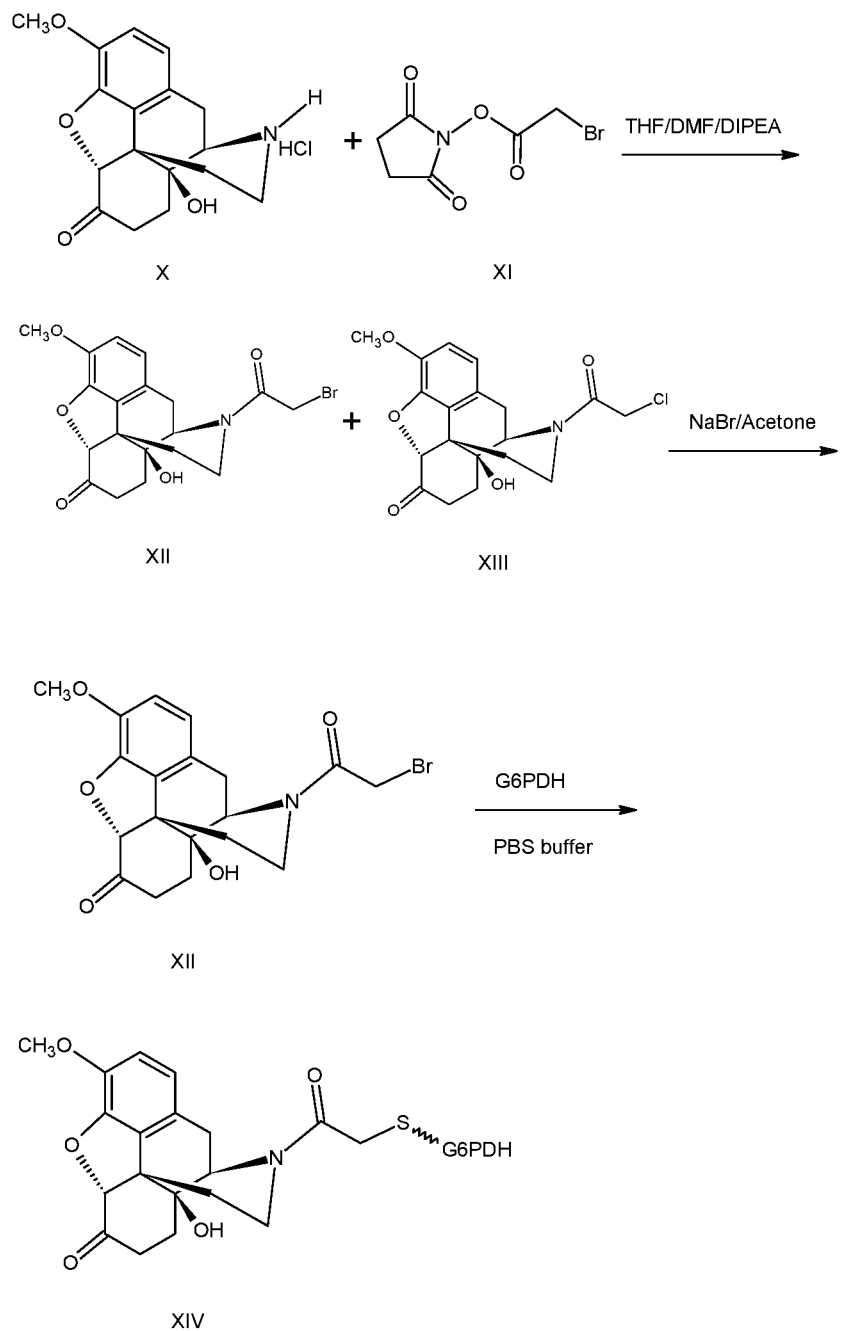
FIG. 5 is a schematic diagram of an example of a synthesis of compounds employed in the compositions and methods in accordance with examples in accordance with the principles described herein.

Definitions mg=milligram
g=gram(s)
ng=nanogram(s)
mL=milliliter(s)
μL=microliter(s)
mmol=millimolar
μmol=micromolar
° C.=degrees Centigrade
min=minute(s)
sec=second(s)
hr=hour(s)
w/v=weight to volume
TLC=thin layer chromatography
HPLC=high performance liquid chromatography
DMF=dimethylformamide
THF=tetrahydrofuran
DTT=dithiothreitol
EDTA=ethylenediaminetetraacetate
DI=deionized
ELISA=enzyme-linked immunosorbent assay
LOCI=luminescent oxygen channeling immunoassay
mIgG=mouse immunoglobulin
MS=mass spectrometry Preparation of Compound of the Formula XII (FIG. 5).

To a stirred solution of noroxycodone (X) (15 mg, 0.0445 mmol) in THF (9 mL) and DMF (1 mL), was added diisopropylethylamine (DIPEA) (45 μL, 0.26 mmol). The reaction was stirred at room temperature for 10 min. Succinimide acetate bromide (XI) (21 mg, 0.089 mmol) was added to the reaction mixture under nitrogen. The reaction mixture was stirred at room temperature for 90 min. TLC analysis of the mixture showed that starting material noroxycodone (X) disappeared, and a new and less polar spot was displayed. Most of THF and DMF were removed by rotary evaporation under reduced pressure. The residue was purified by preparative TLC method, using dichloromethane/ethyl acetate/methanol=5/4/1 as an eluent to give a mixture of noroxycodone chloroacetamide (XIII) and noroxycodone bromoacetamide (XII) (15 mg).

To the stirred solution of XII and XIII (15 mg) in acetone (20 mL), sodium bromide (103 mg, 1 mmol) was added under nitrogen. The reaction was stirred at 56° C. for 24 hr. The reaction was cooled down to room temperature, the solid was removed by filtration, and the filtrate was concentrated by rotary evaporation under reduced pressure. The residue was purified by preparative TLC method, using dichloromethane/ethyl acetate/methanol=5/4/1 as an eluent to give desired noroxycodone bromo-acetamide (XII) (9.7 mg, 51% yield, two steps). FAB-MS: MH$^+$ (422, 424); $^1$H-NMR (CDCl$_3$, 600 MHz) δ: 6.77 (d, J=6 Hz, 1H), 6.68 (d, J=6 Hz, 1H), 5.0 (d, J=6 Hz, 1H), 4.69 (s, 1H), 3.93 (m, 2H), 3.91 (s, 3H), 3.58 (m, 1H), 3.16 (m, 2H), 3.05 (m, 1H), 2.90 (m, 1H), 2.65 (m, 1H), 2.30 (m, 1H), 1.90 (m, 1H), 1.70 (m, 1H), 1.27 (m, 2H).

Preparation of Compound of the Formula XIV (FIG. 5).

A G6PDH enzyme solution (0.53 mL, 19 mg/mL) was buffer-exchanged through G-25 SEPHADEX® column (C16×35) with PBS buffer (50 mM sodium phosphate, 1 mM EDTA, pH 7.25). The concentration of the enzyme was then measured by absorbance at 280 nm and adjusted to 5.0 mg/mL (1.87 mL) with the same buffer solution. DTT (18.7 μL of 0.5 M) was added. The reaction mixture was incubated at 2-8° C. for 16 hr. The protein mixture was purified with 50 mM phosphate 1.0 mM EDTA and 25 μM DTT, pH 7.25 through a G-25 SEPHADEX® column (C16×35). The eluted protein was concentrated by Amicon ultra centrifugal filter (MW cutoff 30,000) to 3.0 mg/mL solution with 50 mM phosphate 1.0 mM EDTA and 25 μM DTT, pH 7.25 buffer. To the above activated protein (1.28 mL, 3 mg/mL) solution, was added 0.742 mg of hapten (compound XII prepared as described above) in DMF solution (128 μL). The slightly turbid reaction mixture was rocked at 2-8° C. for 16 hr. Free hapten (compound XII) was separated from the hapten-enzyme conjugate by pass through a SEPHADEX® G-50 column and eluted with 50 mM phosphate, pH 7.0 buffer. The fractions containing enzyme conjugate were pooled (3.6 mg, 0.34 mg/mL) to give the desired enzyme conjugate XIV.

Figure 6:
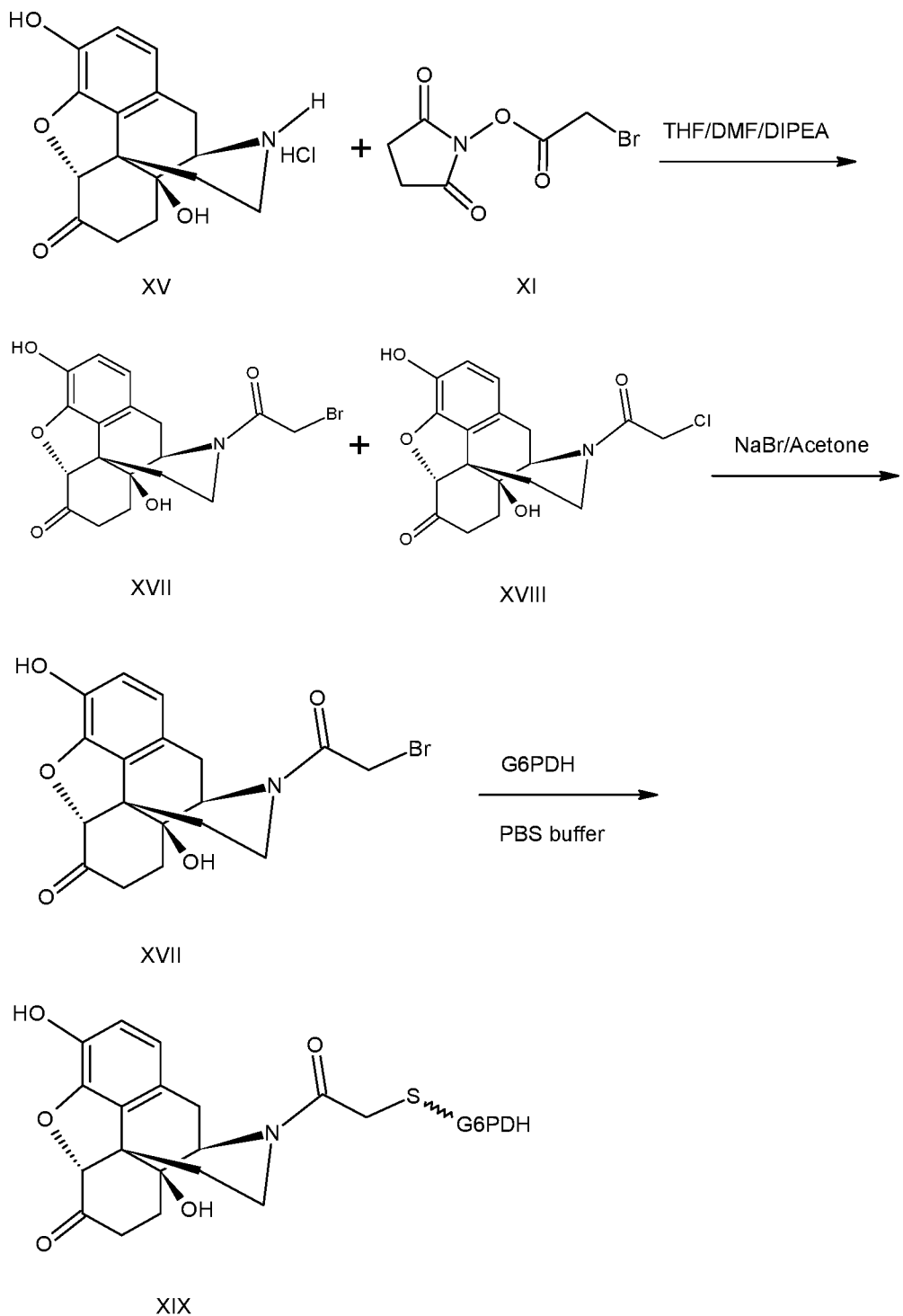
FIG. 6 is a schematic diagram of another example of a synthesis of compounds employed in the compositions and methods in accordance with examples in accordance with the principles described herein.

Preparation of Compound of the Formula XVII (FIG. 6).

To a stirred solution of noroxymorphone (XV) (22.5 mg, 0.0695 mmol) in THF (9 mL) and DMF (1 mL), was added DIPEA (60 µL, 0.34 mmol). The reaction was stirred at room temperature for 5 min. Succinimide acetate bromide (XVI) (19 mg, 0.081 mmol) was added to the reaction mixture under nitrogen. The reaction mixture was stirred at room temperature for 60 min. TLC analysis of the mixture showed that starting material noroxymorphone (XV) disappeared, and a new and less polar spot was displayed. Most of the THF and DMF were removed by rotary evaporation under reduced pressure. The residue was purified by preparative TLC using dichloromethane/ethyl acetate/methanol=5/4/1 as an eluent to give the mixture of noroxymorphone chloroacetamide (XVIII) and noroxymorphone bromoacetamide (XVII) (8.7 mg).

To the stirred solution of XVII and XVIII (8.7 mg) in acetone (20 mL), sodium bromide (103 mg, 1 mmol) was added under nitrogen. The reaction was stirred at 56° C. for 24 hr. The reaction was cooled to room temperature, the solid was removed by filtration, and the filtrate was concentrated by rotary evaporation under reduced pressure. The residue was purified by preparative TLC using dichloromethane/ethyl acetate/methanol=5/4/1 as an eluent to give the desired noroxymorphone bromoacetamide (XVII) (1.3 mg, 5% yield, two steps). FAB-MS: MH$^+$ (408, 410)$^1$H-NMR (CDCl$_3$, 600 MHz); δ: 6.81 (d, J=6 Hz, 1H), 6.68 (d, J=6 Hz, 1H), 6.05 (br, 1H), 5.03 (d, J=6, 1H), 4.71 (s, 1H), 3.92 (m, 2H), 3.72 (m, 1H), 3.16 (m, 1H), 3.10 (m, 2H), 2.90 (m, 1H), 2.65 (m, 1H), 2.35 (m, 1H), 1.92 (m, 1H), 1.73 (m, 1H), 1.27 (m, 2H).

Preparation of Compound of the Formula XIX (FIG. 6).

A G6PDH enzyme solution (0.63 mL, 19 mg/mL) was buffer-exchanged through G-25 SEPHADEX® column (C16×35) with PBS buffer (50 mM sodium phosphate, 1 mM EDTA, pH 7.25). The concentration of the enzyme was then measured by absorbance at 280 nm and adjusted to 5.0 mg/mL (2.1 mL) with the same buffer solution. DTT (21 µL, 0.5 M) was added. The reaction mixture was incubated at 2-8° C. for 16 hr. The protein mixture was purified with 50 mM phosphate 1.0 mM EDTA and 25 µM DTT, pH 7.25 through a G-25 SEPHADEX® column (C16×35). The eluted protein was concentrated by Amicon ultra centrifugal filter (MW cutoff 30,000) to 3.0 mg/mL solution with 50 mM phosphate 1.0 mM EDTA and 25 µM DTT, pH 7.25 buffer. To the above activated protein (1.66 mL, 3 mg/mL) solution, was added 0.93 mg of hapten compound XVII in DMF solution (93 µL). Slightly turbid reaction mixture was rocked at 2-8° C. for 16 hr. Free hapten XVII was separated from the hapten-enzyme conjugate XIX by pass through a SEPHADEX® G-50 column, eluted with 50 mM phosphate, pH 7.0 buffer. The fractions containing enzyme conjugate XIX were pooled (4.2 mg, 0.37 mg/mL) to give the desired enzyme conjugate XIX.

Figure 7:
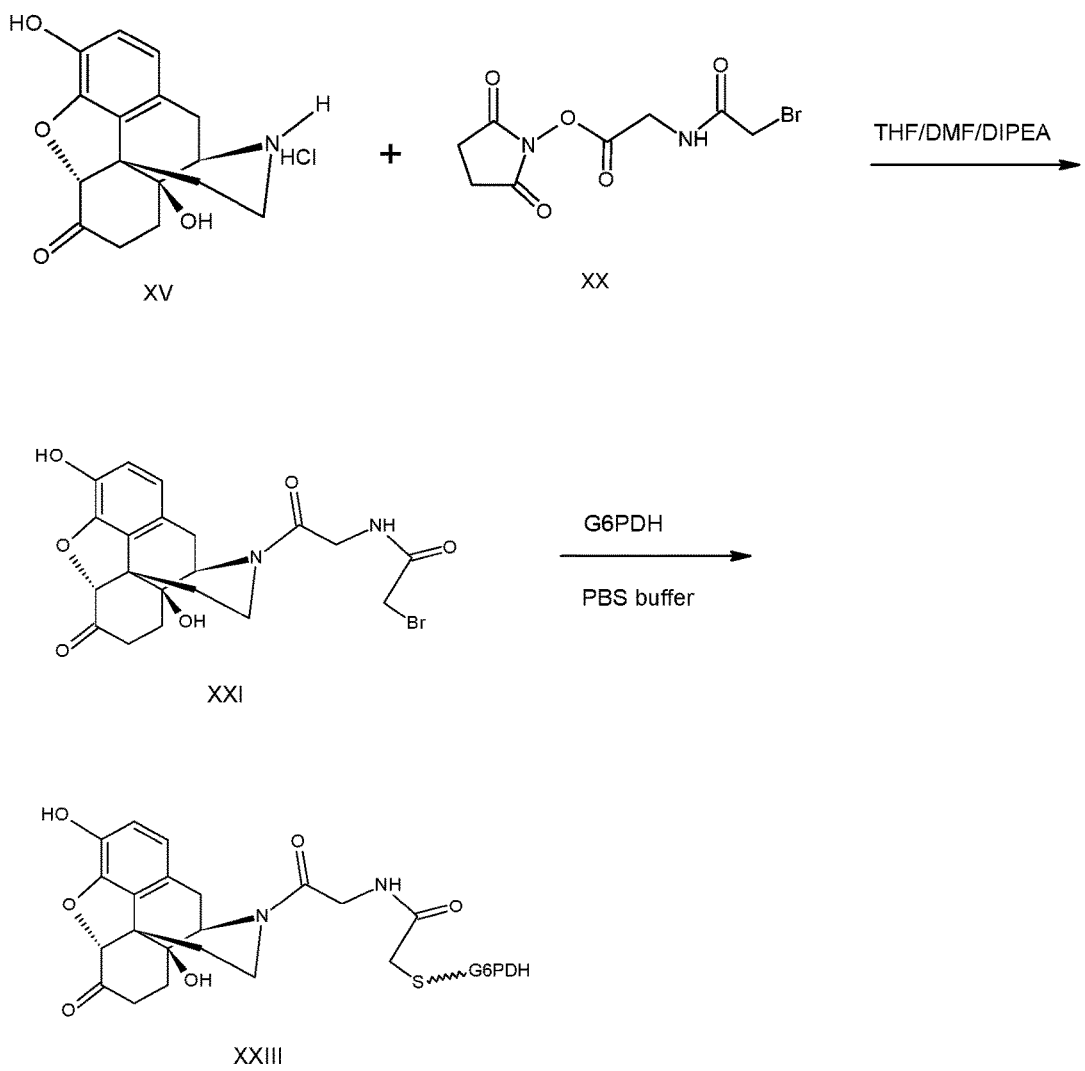
FIG. 7 is a schematic diagram of another example of a synthesis of compounds employed in the compositions and methods in accordance with examples in accordance with the principles described herein.

Preparation of Compound of the Formula XXI (FIG. 7).

To a high vacuum dried noroxymorphone hydrochloride (XV) (20.0 mg, 0.061 mmol) in THF (3 mL) and DMF (0.5 mL) solution was added DIPEA (53.25 µl, 0.305 mmol, 5 equivalents). The reaction mixture was stirred under nitrogen atmosphere for 30 min before BA glycine NHS ester XX (35.8 mg, 0.122 mmol, 2 equivalents) was added. The reaction was stirred at room temperature under nitrogen atmosphere for 80 min. Progress of the reaction was monitored with TLC using 20% methanol in dichloromethane and product is a spot less polar than that of BA glycine NHS ester XX. Most of the solvent was removed by rotary evaporator under reduced pressure. Crude product was purified by HPLC with SB-C18 (250×21.2, Agilent Technologies) column using 0.1% formic acid in water/0.1% formic acid in methanol as the eluent solvent system to give desired product noroxymorphone bromoacetamide XXI (16.2 mg, 19.3% yield). Mass spectrum, ES, m/e: MH$^+$, 465, 467.

Preparation of Compound of the Formula XXIII (FIG. 7).

A G6PDH enzyme solution (0.6 mL, 21.1 mg/mL) was buffer-exchanged through an Amicon Ultra centrifugal filter (Ultracel-30K, EMD Millipore, Billerica Mass.) with PBS buffer (50 mM sodium phosphate, 1 mM EDTA, pH 7.25). The concentration of the enzyme was then measured by absorbance at 280 nm and adjusted to 5.0 mg/mL (1.55 mL) with the same buffer solution. DTT (0.5 M, 15.5 µL) was added into the enzyme solution and the mixture was rocked at 2-8° C. for 16 hr. Excess DTT was removed by a G-25 SEPHADEX® column pre-equilibrated with 50 mM sodium phosphate, 1 mM EDTA, 25 µM DTT, pH 7.25 buffer. The concentration of the purified protein was measured by absorbance at 280 nm and adjusted to 3 mg/mL (2.52 mL) with PBS buffer (50 mM sodium phosphate, 1 mM EDTA, 25 µM DTT, pH 7.25). Noroxymorphone bromoacetamide XXI (4.0 mg), prepared as described above, in DMF (0.267 mL) was added into the activated enzyme (1.26 mL, 3 mg/mL) and the solution was rocked in a cold room (4° C.) for 16 hr. G6PDH conjugate XXIII was purified by a pre-equilibrated column (SEPHADEX® G-50) eluted with sodium phosphate buffer (50 mM sodium phosphate, pH 7.0). The fractions containing enzyme conjugate XXIII were pooled (3.9 mg, 0.36 mg/mL) to give the desired enzyme conjugate XXIII.

Figure 8:
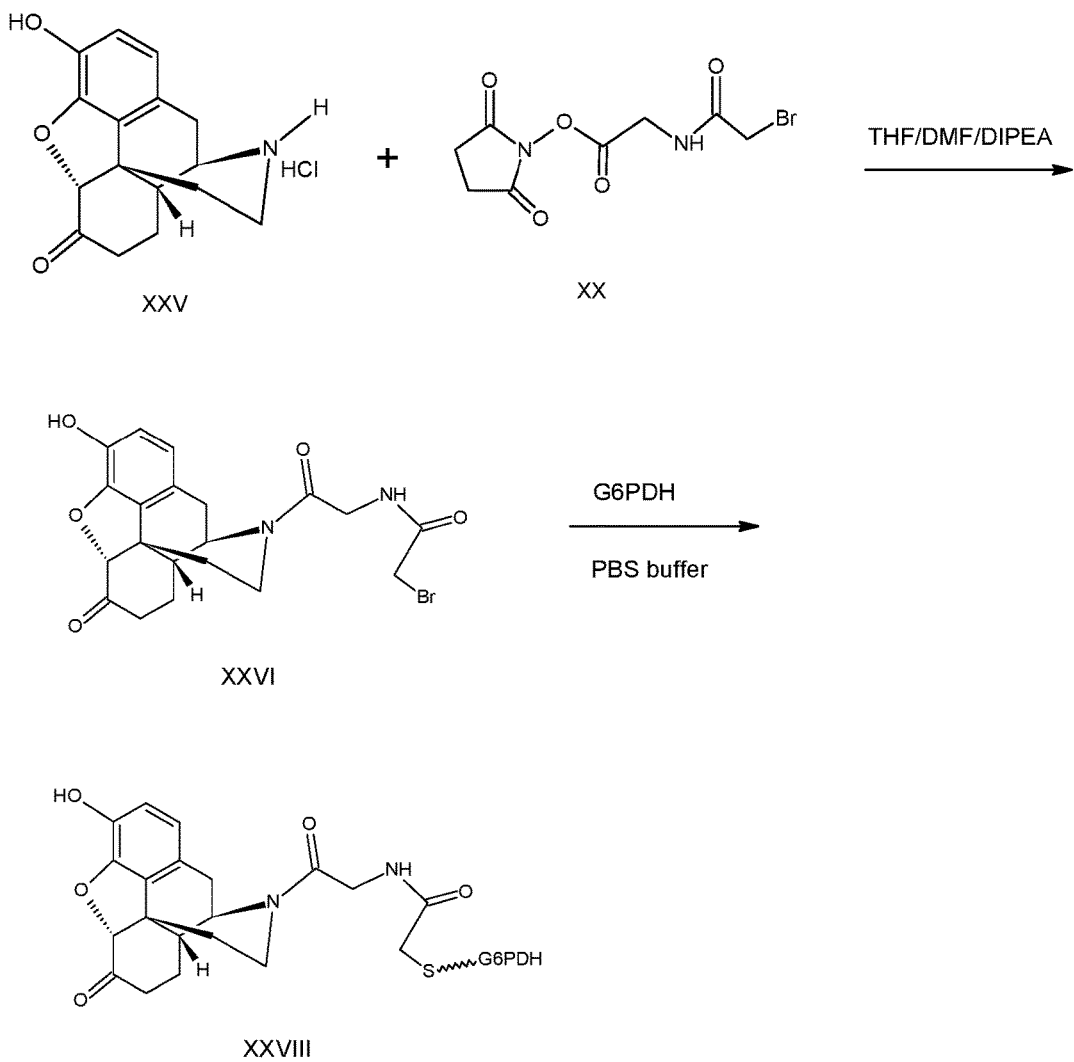
FIG. 8 is a schematic diagram of another example of a synthesis of compounds employed in the compositions and methods in accordance with examples in accordance with the principles described herein.

Preparation of Compound of the Formula XXVI (FIG. 8).

To a high vacuum dried norhydromorphone hydrochloride (50.0 mg, 0.147 mg) in THF (4.5 mL) and DMF (2 mL) solution was added DIPEA (154 µl, 0.882 mmol, 6 equivalents). The reaction mixture was stirred under nitrogen atmosphere for 20 min before BA glycine NHS ester XX (86.2 mg, 0.294 mmol, 2 equivalents) was added. The reaction was stirred at room temperature under nitrogen atmosphere for 100 min. Progress of the reaction was monitored with TLC using 20% methanol in dichloromethane and product was a spot less polar than that of XX. The reaction mixture was concentrated using a rotary evaporator to remove most of the solvent. Crude (210.3 mg) product was purified by HPLC with SB-C18 (250×21.2, Agilent Technologies) column using 0.1% formic acid in DI water/ 0.1% formic acid in methanol as the solvent system to give desired product (XXVI) (3.3 mg, 4% yield). Mass spectrum, ES, m/e: MH$^+$, 449, 451.

Preparation of Compound of the Formula XXVIII (FIG. 8).

A G6PDH enzyme solution (0.6 mL, 21.1 mg/mL) was buffer-exchanged through an Amicon Ultra centrifugal filter (EMD Millipore, Ultracel-30K) with PBS buffer (50 mM sodium phosphate, 1 mM EDTA, pH 7.25). The concentration of the enzyme was then measured by absorbance at 280 nm and adjusted to 5.0 mg/mL (1.55 mL) with the same buffer solution. DTT (0.5 M, 15.5 L) was added into the enzyme solution and the mixture was rocked at 2-8° C. for 16 hr. Excess DTT was removed by a G-25 SEPHADEX® column pre-equilibrated with 50 mM sodium phosphate, 1 mM EDTA, 25 µM DTT, pH 7.25 buffer. The concentration of the purified protein was measured by absorbance at 280 nm and adjusted to 3 mg/mL (2.52 mL) with PBS buffer (50 mM sodium phosphate, 1 mM EDTA, 25 µM DTT, pH 7.25). Norhydromorphone bromoacetamide (XXVI) (3.3 mg) in DMF (0.20 mL) was added into the activated enzyme (0.9 mL, 3 mg/mL) and the solution was rocked in cold room (4° C.) for 16 hr. G6PDH conjugate was purified by a pre-equilibrated column (SEPHADEX® G-50) eluted with sodium phosphate buffer (50 mM sodium phosphate, pH 7.0). The fractions containing enzyme conjugate XXVIII were pooled (2.53 mg, 0.24 mg/mL) to give the desired enzyme conjugate XXVIII.

Figure 9:
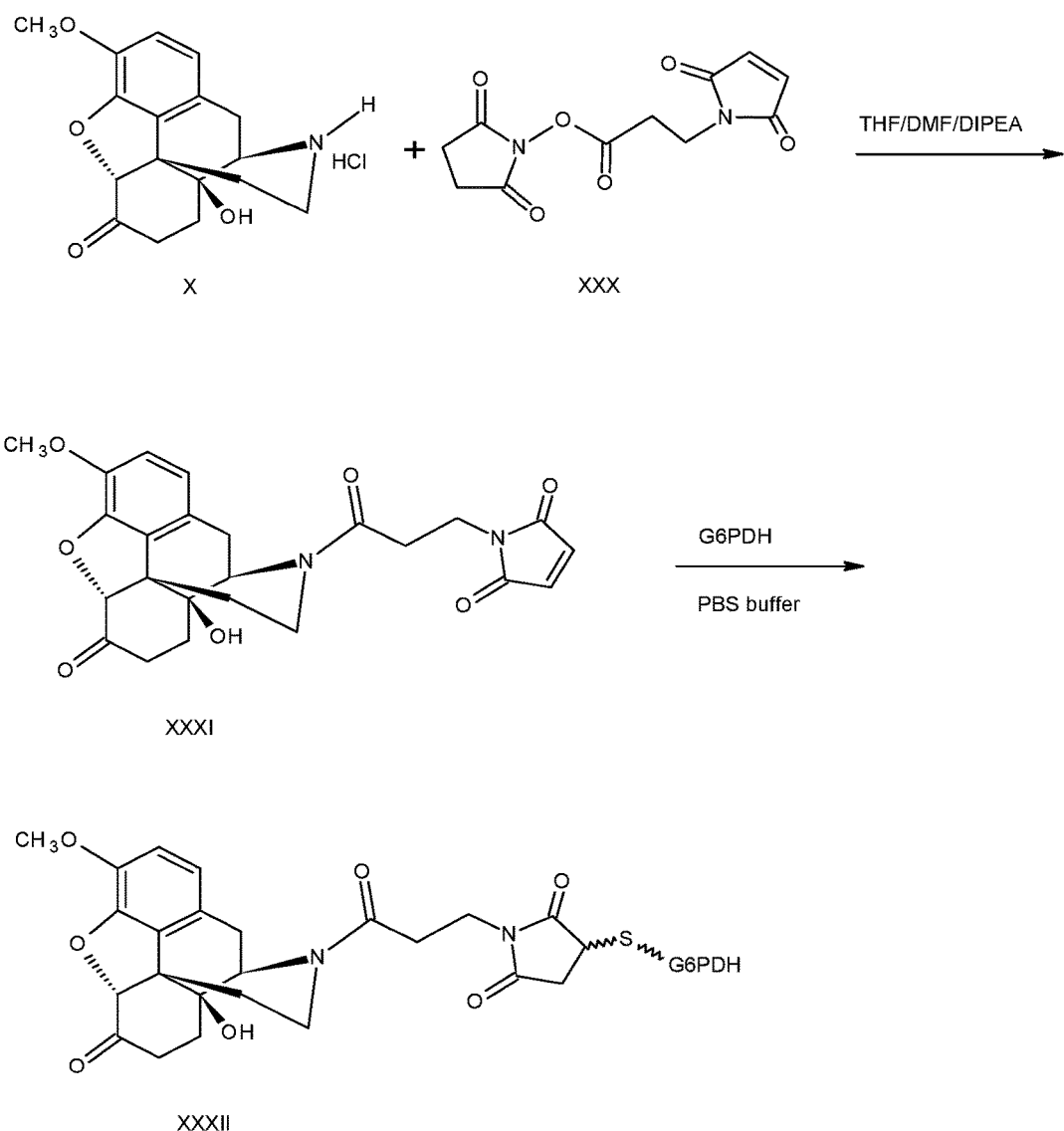
FIG. 9 is a schematic diagram of another example of a synthesis of compounds employed in the compositions and methods in accordance with examples in accordance with the principles described herein.

Preparation of Compound of the Formula XXXI (FIG. 9).

To a stirred solution of noroxycodone hydrochloride (X) (10.7 mg, 0.0317 mmol) in THF (9 mL) and DMF (1 mL), was added DIPEA (35 µL, 0.2 mmol). The reaction was stirred at room temperature for 5 min. and 3-maleimidepropionic acid N-hydroxy succinimide (13 mg, 0.049 mmol) was added to the reaction mixture under nitrogen. The reaction mixture was stirred at room temperature for 90 min. TLC analysis of the mixture showed that starting material noroxycodone X disappeared, and a new and less polar spot was displayed. Most of the THF and DMF were removed by rotary evaporation under reduced pressure. The residue was purified by preparative TLC method, using dichloromethane/ethyl acetate/methanol=5/4/1 as an eluent to give the desired product noroxycodone maleimide XXXI (10.0 mg, 70% yield); FAB-MS: MH$^+$ (453); $^1$H-NMR (CDCl$_3$, 600 MHz) δ: 6.74 (m, 1H), 6.72 (s, 2H), 6.65 (m, 1H), 5.02 (m, 1H), 4.69 (m, 1H), 3.92 (s, 3H), 3.90 (m, 2H), 3.63 (m, 1H), 3.05 (m, 4H), 2.83 (m, 1H), 2.64 (m, 1H), 2.53 (m, 1H), 2.31 (m, 1H), 1.91 (m, 1H), 1.72 (m, 1H), 1.27 (m, 2H).

Preparation of Compound of the Formula XXXII (FIG. 9).

A G6PDH enzyme solution (0.53 mL, 19 mg/mL) was buffer-exchanged through a G-25 SEPHADEX® column (C16×35) with PBS buffer (50 mM sodium phosphate, 1 mM EDTA, pH 7.25). The concentration of the enzyme was then measured by absorbance at 280 nm and adjusted to 5.0 mg/mL (1.87 mL) with the same buffer solution. DTT (18.7 µL of 0.5 M) was added. The reaction mixture was incubated at 2-8° C. for 16 hr. The protein mixture was purified with 50 mM phosphate 1.0 mM EDTA and 25 µM DTT, pH 7.25 through a G-25 SEPHADEX® column (C16×35). The eluted protein was concentrated by Amicon ultra centrifugal filter (MW cutoff 30,000) to 3.0 mg/mL solution with 50 mM phosphate 1.0 mM EDTA and 25 µM DTT, pH 7.25 buffer. To the above activated protein (1.3 mL, 3 mg/mL) solution was added 0.80 mg of noroxycodone maleimide hapten XXXI (prepared as described above) in DMF solution (130 µL). A slightly turbid reaction mixture was rocked at 2-8° C. for 16 hr. Free hapten XXXI was separated from hapten-enzyme conjugate XXXII by passage through a SEPHADEX® G-50 column, eluted with 50 mM phosphate, pH 7.0 buffer. The fractions containing enzyme conjugate XXXII were pooled (3.5 mg, 0.33 mg/mL) to give the desired conjugate XXXII.

Figure 10:
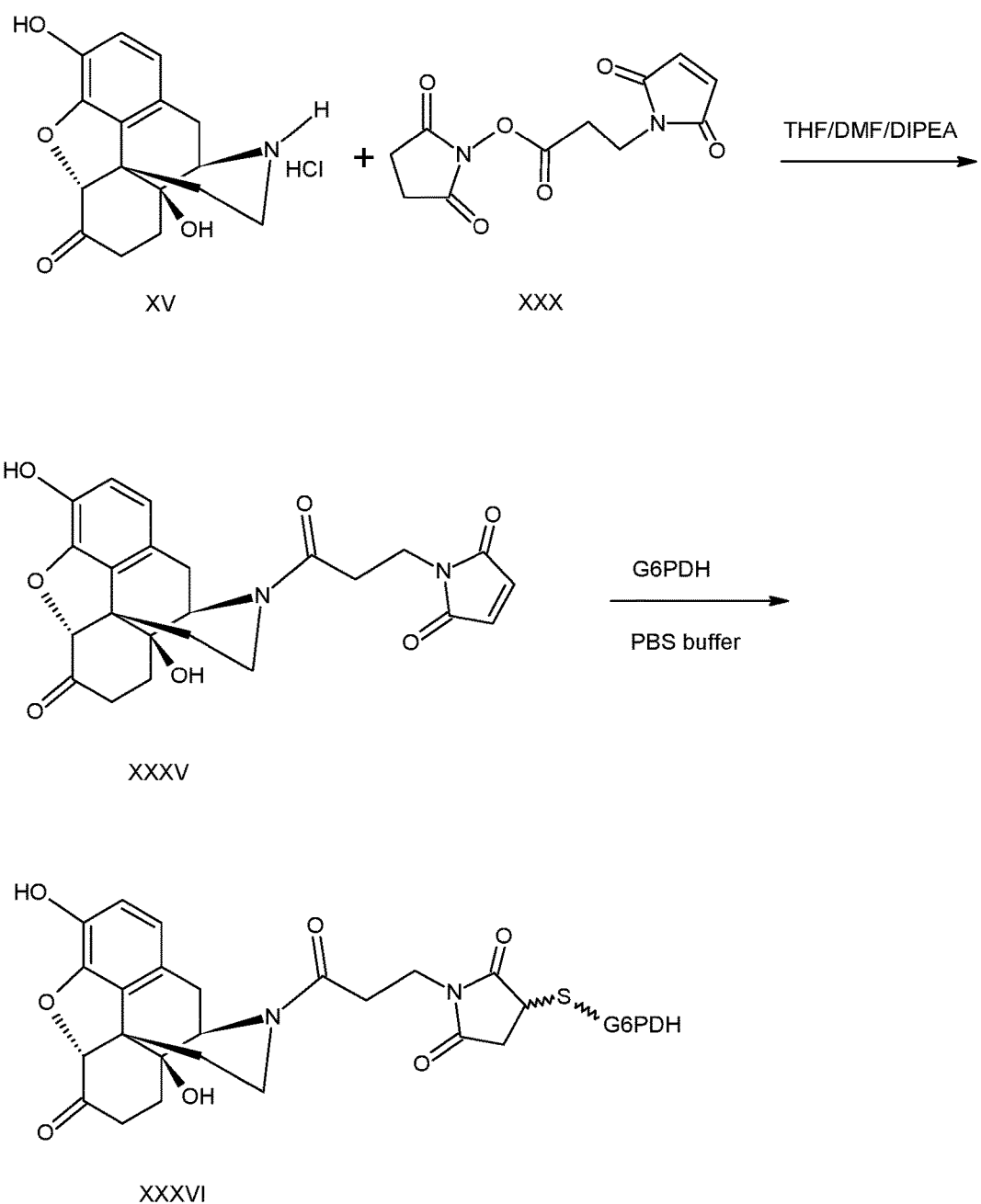
FIG. 10 is a schematic diagram of another example of a synthesis of compounds employed in the compositions and methods in accordance with examples in accordance with the principles described herein.

Preparation of Compound of the Formula XXXV (FIG. 10).

To a stirred solution of noroxymorphone hydrochloride (XV) (15.5 mg, 0.048 mmol) in THF (9 mL) and DMF (1 mL) was added DIPEA (50 µL, 0.287 mmol). The reaction was stirred at room temperature for 10 minutes. 3-maleimidepropanic acid N-hydroxy succinimide XXX (19.8 mg, 0.075 mmol) was added to the reaction mixture under nitrogen. The reaction mixture was stirred at room temperature for 90 min. TLC analysis of the mixture showed that starting material noroxymorphone XV disappeared, and a new and less polar spot was displayed. Most of the THF and DMF were removed by rotary evaporation under reduced pressure. The residue was purified by preparative TLC method using dichloromethane/ethyl acetate/methanol=5/4/1 as an eluent to give the desired product noroxymorphone maleimide (XXXV) (17.2 mg, 82% yield). FAB-MS: MH$^+$ (439); $^1$H-NMR (CDCl$_3$, 600 MHz) δ: 6.76 (m, 1H), 6.72 (m, 2H), 6.64 (m, 1H), 6.07 (m, 1H), 5.02 (m, 1H), 4.70 (m, 1H), 3.91 (m, 2H), 3.62 (m, 1H), 3.06 (m, 3H), 2.82 (m, 2H), 2.62 (m, 1H), 2.57 (m, 1H), 2.30 (m, 1H), 1.92 (m, 1H), 1.67 (m, 1H), 1.26 (m, 2H).

Preparation of Compound of the Formula XXXVI (FIG. 10).

A G6PDH enzyme solution (0.63 mL, 19 mg/mL) was buffer-exchanged through a G-25 SEPHADEX® column (C16×35) with PBS buffer (50 mM sodium phosphate, 1 mM EDTA, pH 7.25). The concentration of the enzyme was then measured by absorbance at 280 nm and adjusted to 5.0 mg/mL (2.1 mL) with the same buffer solution. DTT (21 µL, 0.5 M) was added. The reaction mixture was incubated at 2-8° C. for 16 hr. The protein mixture was purified with 50 mM phosphate 1.0 mM EDTA and 25 µM DTT, pH 7.25 through a G-25 SEPHADEX® column (C16×35). The eluted protein was concentrated by Amicon ultra centrifugal filter (MW cutoff 30,000) to 3.0 mg/mL solution with 50 mM phosphate 1.0 mM EDTA and 25 µM DTT, pH 7.25 buffer. To the above activated protein (1.66 mL, 3 mg/mL) solution was added 1.0 mg of noroxymorphone maleimide hapten (XXXV) in DMF solution (100 µL). The slightly turbid reaction mixture was rocked at 2-8° C. for 16 hr. Free hapten XXXV was separated from the hapten-enzyme conjugate XXXVI by passage through a SEPHADEX® G-50 column, eluted with 50 mM phosphate, pH 7.0 buffer. The fractions containing enzyme conjugate XXXVI were pooled (4.4 mg, 0.36 mg/mL) to give the desired enzyme conjugate XXXVI.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A compound of the Formula I:

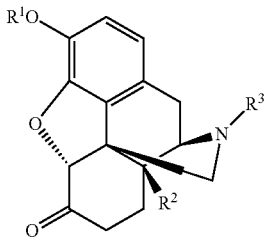

wherein:
- $R^1$ is H or lower alkyl,
- $R^2$ is H or OH, and
- $R^3$ is —C(O)—(CH$_2$)$_a$—(NH—C(O)—(CH$_2$)$_b$)$_c$R$^4$, wherein a is an integer from 1 to 10, b is an integer from 1 to 10 and c is 0 or an integer from 1 to 5, and wherein $R^4$ is halogen, an immunogenic carrier, or a label; or

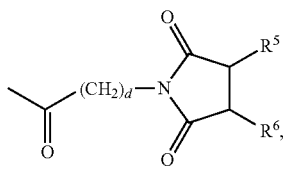

wherein $R^5$ is an immunogenic carrier or a label and $R^6$ is H, or wherein $R^5$ and $R^6$ are taken together to form a carbon-carbon double bond; and wherein said label is selected from the group consisting of a fluorescent label, a chemiluminescent label and a protein label.

2. The compound according to claim 1 wherein $R^4$ is an enzyme label.

3. The compound according to claim 2 wherein the enzyme is glucose-6-phosphate dehydrogenase, alkaline phosphatase, B-galactosidase or horse radish peroxidase.

4. The compound according to claim 3 wherein the enzyme is glucose-6-phosphate dehydrogenase and $R^3$ is —C(O)—(CH$_2$)$_a$—(NH—C(O)—(CH$_2$)$_b$)$_c$R$^4$ wherein a is 1 and c is 0 and the glucose-6-phosphate dehydrogenase is attached through a sulfur atom of the glucose-6-phosphate dehydrogenase.

5. The compound according to claim 3 wherein the enzyme is glucose-6-phosphate dehydrogenase and $R^3$ is —C(O)—(CH$_2$)$_a$—(NH—C(O)—(CH$_2$)$_b$)$_c$R$^4$ wherein a is 1, b is 1 and c is 1 and the glucose-6-phosphate dehydrogenase is attached through a sulfur atom of the glucose-6-phosphate dehydrogenase.

6. The compound according to claim 3 wherein the enzyme is glucose-6-phosphate dehydrogenase and $R^3$ is

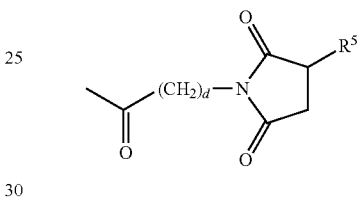

wherein d is 2 and the glucose-6-phosphate dehydrogenase is attached through a sulfur atom of the glucose-6-phosphate dehydrogenase.

* * * * *